US006558934B1

(12) United States Patent
Clausen et al.

(10) Patent No.: US 6,558,934 B1
(45) Date of Patent: May 6, 2003

(54) **UDP-GALACTOSE: β-*N*-ACETYL-GLUCOSAMINE β-1,4-GALACTOSYL-TRANSFERASE, β4GAL-T2**

(75) Inventors: Henrik Clausen, Holte (DK); Eric Paul Bennett, Lyngby (DK)

(73) Assignee: Glycozm APS, Holte (DK)

( * ) Notice: Subject to any disclaimer, the term of this patent is extended or adjusted under 35 U.S.C. 154(b) by 0 days.

(21) Appl. No.: 09/118,464

(22) Filed: Jul. 17, 1998

(51) Int. Cl.[7] .......................... C12P 21/06; C12N 9/00; C12N 9/10; C12N 1/20; C12N 15/00

(52) U.S. Cl. ...................... 435/193; 435/183; 435/69.1; 435/252.3; 435/320.1; 435/325; 536/23.2

(58) Field of Search ................................ 435/183, 193, 435/69.1, 252.3, 325, 320.1; 536/23.2

(56) References Cited

FOREIGN PATENT DOCUMENTS

WO WO 90/07000 * 6/1990

OTHER PUBLICATIONS

Lo et al. Gen Bank Accession No. AF038660, May 14, 1998.*

Almeida et al. GenBank Accession No. Y12510, Mar. 31, 1998.*

Hillier et al. EST Database Accession No. AA453005, Jun. 5, 1997.*

Uehera et al. Molecular cloning and characterization of β1,4–galactosyltransferase expressed in mouse testis. 1997, Eur. J. Biochem. vol. 244:706–712, Mar. 1997.*

Sudo et al. GenBank Accession No. D31327, dated Feb. 8, 1995, Mar. 1997.*

Almeida et al., Glycoconjugate J. 1997, 14:S44.

Lo et al., Glycobiology 1998, 8:517–526.

* cited by examiner

*Primary Examiner*—Rebecca E. Prouty
*Assistant Examiner*—Manjunath N. Rao
(74) *Attorney, Agent, or Firm*—Darby & Darby

(57) ABSTRACT

A novel gene defining a novel enzyme in the UDP-D-galactose: β-N-acetyl-glucosamine β-1,4-galactosyltransferase family, termed β4Gal-T2, with unique enzymatic properties is disclosed. The enzymatic activity of β4Gal-T2 is shown to be distinct from that of previously identified enzymes of this gene family. The invention discloses isolated DNA molecules and DNA constructs encoding β4Gal-T2 and derivatives thereof by way of amino acid deletion, substitution or insertion exhibiting β4Gal-T2 activity, as well as cloning and expression vectors including such DNA, cells transfected with the vectors, and recombinant methods for providing β4Gal-T2. The enzyme β4Gal-T2 and β4Gal-T2-active derivatives thereof are disclosed, in particular soluble derivatives comprising the catalytically active domain of β4Gal-T2. Further, the invention discloses methods of obtaining β-1,4-galactosyl glycosylated saccharides, glycopeptides or glycoproteins by use of an enzymically active β4Gal-T2 protein or fusion protein thereof or by using cells stably transfected with a vector including DNA encoding an enzymatically active β4Gal-T2 protein as an expression system for recombinant production of such glycopeptides or glycoproteins. Also a method for the identification of DNA sequence variations in the β4Gal-T2 gene by isolating DNA from a patient, amplifying β4Gal-T2-coding exons by PCR, and detecting the presence of DNA sequence variation, are disclosed.

18 Claims, 9 Drawing Sheets

FIG. 2

β4Gal-T2

```
-169  .........................AGCCTGGTCCCAGTTGGCCTGCCCTGCTTGTCGCTGGGATCTGAATGACCAAACCACTTCCCACCATGGCTCCTGGAAGGACTAAATGAAGTCA  -74

                                                                                        M  S  R  L  L  G  G  T  L  E  R  V  C  K  A    15
-75   TGAGTATAAAGTGCTCCTGCATGGCCAGCAGCCGGATGCCCGGGCCCACTGGGCGGGCCAGTGGCCGCTTGCGGGATGAGCAGACTGCTGGGGGGGACGCTGGAGCGCGTCTGCAAGGCT   45

16    V  L  L  L  C  L  L  H  F  L  V  A  V  I  L  Y  F  D  V  Y  A  Q  H  L  A  F  F  S  R  F  S  A  R  G  P  A  H  A  L  H    55
46    GTGCTCCTTCTCTGCCTGCTGCACTTCCTCGTGGCCGTCATCCTCTACTTTGACGTCTACGCCCAGCACCTGGCCTTCTTCAGCCGCTTCAGTGCCCGAGGCCCTGCCCATGCCCTCCAC  165

56    P  A  A  S  S  S  S  S  S  S  N* C  S  R  P  N* A  T  A  S  S  S  G  L  P  E  V  P  S  A  L  P  G  P  T  A  P  T  L  P    95
166   CCAGCTGCTAGCAGCAGCAGCAGCAGCAGCAACTGCTCCCGGCCCAACGCCACCGCCTCTAGCTCCGGGCTCCCTGAGGTCCCCAGTGCCCTGCCCGGTCCCACGGCTCCCACGCTGCCA  285

96    P  C  P  D  S  P  P  G  L  V  G  R  L  L  I  E  F  T  S  P  M  P  L  E  R  V  Q  R  E  N  P  G  V  L  M  G  G  R  Y  T   135
286   CCCTGTCCTGACTCGCCACCTGGTCTTGTGGGCAGACTGCTGATCGAGTTCACCTCACCCATGCCCCTGGAGCGGGTGCAGAGGGAGAACCCAGGCGTGCTCATGGGCGGCCGATACACA  405

136   P  P  D  C  T  P  A  Q  T  V  A  V  I  I  P  F  R  H  R  E  H  H  L  R  Y  W  L  H  Y  L  H  P  I  L  R  R  Q  R  L  R   175
406   CCGCCCGACTGCACCCCAGCCCAGACGGTGGCGGTCATCATCCCCTTTAGACACCGGGAACACCACCTGCGCTACTGGCTCCACTATCTACACCCCATCTTGAGGCGGCAGCGGCTGCGC  525

176   Y  G  V  Y  V  I  N  Q  H  G  E  D  T  F  N  R  A  K  L  L  N  V  G  F  L  E  A  L  K  E  D  A  A  Y  D  C  F  I  F  S   215
526   TACGGCGTCTATGTCATCAACCAGCATGGTGAGGACACCTTCAACCGGGCCAAGCTGCTTAACGTGGGCTTCCTAGAGGCGCTGAAGGAGGATGCCGCCTATGACTGCTTCATCTTCAGC  645

216   D  V  D  L  V  P  M  D  D  R  N  L  Y  R  C  G  D  Q  P  R  H  F  A  I  A  M  D  K  F  G  F  R  L  P  Y  A  G  Y  F  G   255
646   GATGTGGACCTGGTCCCCATGGATGACCGCAACCTATACCGCTGCGGCGACCAACCCCGCCACTTTGCCATTGCCATGGACAAGTTTGGCTTCCGGCTTCCCTATGCTGGCTACTTTGGA  765

256   G  V  S  G  L  S  K  A  Q  F  L  R  I  N  G  F  P  N  E  Y  W  G  W  G  G  E  D  D  D  I  F  N  R  I  S  L  T  G  M  K   295
766   GGTGTGTCAGGCCTGAGTAAGGCTCAGTTTCTGAGAATCAATGGCTTCCCCAATGAGTACTGGGGCTGGGGTGGCGAGGATGATGACATCTTCAACCGGATCTCCCTGACTGGGATGAAG  885

296   I  S  R  P  D  I  R  I  G  R  Y  R  M  I  K  H  D  R  D  K  H  N  E  P  N  P  Q  R  F  T  K  I  Q  N  T  K  L  T  M  K   335
886   ATCTCACGCCCAGACATCCGAATCGGCCGCTACCGCATGATCAAGCACGACCGCGACAAGCATAACGAACCTAACCCTCAGAGGTTTACCAAGATTCAAAACACGAAGCTGACCATGAAG  1005

336   R  D  G  I  G  S  V  R  Y  Q  V  L  E  V  S  R  Q  P  L  F  T  N* I  T  V  D  I  G  R  P  P  S  W  P  P  R  G  *            372
1006  CGGGACGGCATTGGGTCAGTGCGGTACCAGGTCTTGGAGGTGTCTCGGCAACCACTCTTCACCAATATCACAGTGGACATTGGGCGGCCTCCGTCGTGGCCCCCTCGGGGCTGACACTAA  1125

1126  TGGACAGAGGCTCTCGGTGCCGAAGATTGCCTGCCAGAGGACTGACCACAGCCTGGCTGGCAGCTGCTCTGTGGAGGACCTCCAGGACTGAGACTGGGCTCTGTTTTCCAAGGGTCTTCA  1245
1246  CTAGGCCCCCTAGCTACACCTGGAAGTTTCAGAACCCACTTTGGGGGGCCTCCTGCCTGGGCAGGCTCTTCAAGTGTGGCCCTCTTTGGAGTCAACCCTCCTTCCCGACCCCCTCCCCCT  1365
1366  AGCCCAGCCCCAGTCACTGTCAGGGTCGGCCAGCCCCTGCACTGCCTCGCAGAGTGGCCTGGGCTAGGTCACTCCACCTCTCTGTGCCTCAGTTTCCCCCCCTTGAGTCCCCTAGGGCC  1485
1486  TGGAAGGGTGGGAGGTATGTCTAGGGGGCAGTGTCTCTTCCAGGGGGAATTCTCAGCTCTTGGGAACCCCCTTGCTCCCAGGGGAGGGGAAACCTTTTTCATTCAACATTGTAGGGGGCA  1605
1606  AGCTTTGGTGCGCCCCCTGCTGAGGAGCAGCCCCAGGAGGGGACCAGAGGGGATGCTGTGTCGCTGCCTGGGATCTTGGGGTTGGCCTTTGCATGGAGGCAGGTGGGGCTTGGATCAGT  1725
1726  AAGTTTGGTTCCCGCCTCCCTGTTTGAGAGAGGAGGCAGGAGCCCCAGGGCCGGCTTGTGTTTGTACATTGCACAGAAACTTGTGTGGGTGCTTTAGTAAAAAACGTGAATGGAAAAAAA  1845
1846  AAAAAAAAAAAAA                                                                                                                1858
```

```
b4Gal-T1    :        MRLREPLLSGAAMPGASLQRACRLLVAVCVWHLGVTLVYYLAGR
Chick1      :           MKEP-----ALPGTSLQRACRLLVAFCALHLSATLLYYLAGS
b4Gal-T2    :                      MSRLLGGTLERVCKAVLLLCLLHFLVAVILYFDVY
Chick2      :                    MTRLLLGVTLERICKAVLLLCLLHFVIIMILYFDVY
b4Gal-T3    :                          MLRRLLERPCTLALLVG---SQLAVMMYLSLG
b4GlcNAc-T  : MYLVVCWGRVTGNMISTRHCFSRCKSRSVRVIKATAMLFVAAMLFLALHMN

b4Gal-T1    : ---DSSPVVDSGPGPASNLTSVPVPHTTALSLPACPEESPLLVGPMLIEFN
Chick1      : ------PVSAQ---PRN------LPDSAPSGL--CPDPSPLLVGPLRVEFS
b4Gal-T2    : -----LPEVPS-ALPGP----------TAPTLPPCPDSPPGLVGRLLIEFT
Chick2      : -----EPPSPS-AKPNTN------RSVTEKPLQPCQEMPSGLVGRLLIEFS
b4Gal-T3    : -----APGGPP----------------APQGLPYCPERSPLLVGPVSVSFS
b4GlcNAc-T  : QRNEVIACSDTSEEFRTD-SKRITLVNSQSGVP-CPIRPPALAGRFVPSKK

b4Gal-T1    : QLDYGIYGIYVINQAGDTIFNRAKLLNVGFQEALK-DYDYTCFVFSDVDLI
Chick1      : QLDY---GVYVINQDGDEEFNRAKLLNVGFTEALK-EYDYDCFVFSDVDLI
b4Gal-T2    : RLRY---GVYVINQHGEDTFNRAKLLNVGFLEALKEDAAYDCFIFSDVDLV
Chick2      : KVAY---GIYIINQYGEDTFNRAKLLNVGFLEALKDDEEYDCFIFSDVDLI
b4Gal-T3    : QLAY---GIYVIHQAGNGTFNRAKLLNVGVREALR-DEEWDCLFLHDVDLL
b4GlcNAc-T  : NVDF---TIFVIEQTTPETFNKGILFNAGYLEALKVDN-YDCFILHDVDMI

b4Gal-T1    : GGEDDDIFNRLVFRGMSISRPNAVVGRCRMIRHSR----------------
Chick1      : GGEDDDIYNRLVFKGMGISRPDAVIGKCRMIRHSR----------------
b4Gal-T2    : GGEDDDIFNRISLTGMKISRPDIRIGRYRMIKHDR----------------
Chick2      : GGEDDDIFNRISLNGMKVSRPDIRMGRYRMIKHER----------------
b4Gal-T3    : GGEDDDIATRVRLAGMKISRPPTSVGHYKMVKHRG----------------
b4GlcNAc-T  : GGEDDDLRNRAVHMKLPLLRKTLAHGLYDMVSHVEAGWNVNPHSKGAHSLY

b4Gal-T1    : GLNSLTYQVLDVQRYPLYTQITVDIGT------------------------
Chick1      : GLNSLSYEVLRTDRFPLYTRITVDIGA------------------------
b4Gal-T2    : GIGSVRYQVLEVSRQPLFTNITVDIGR------------------------
Chick2      : GISSLQYRLVEVSRQPMYTNITVEIGR------------------------
b4Gal-T3    : GMNSLTYQLLARELGPLYTNITADIGTDPRGPRAPSGPRYPPGSSQAFRQE
b4GlcNAc-T  : GINSLVYNVTWYRTSPLYTWVGVGFNKTVITN-------------------
```

```
DLS-----RLPQLVGVSTPLQGG-SNSAAAIGQSSGELRTGGARPPPPLGASSQPRPGG :  97
SLTPP---RSPEPPPRRPPP----AN--LSLPPS---------RPPPPPAAR--PRPG- :  75
AQHLA---FFSRFSARGPAHALH-PAASSSSSSN-------CSRPNATASSSG----- :  78
AQHLD---FFSRFNARN-TSRVH-PFSNSS--------------RPNSTAPSYGPRGA- :  75
GFR-----SLSALFGRD----QG-PTFDYS--------------HPRDVYSNLSHLPG- :  63
FSHEASQQNLHRAAPISSPTTISRSTVQIRNATHDFLPASSTPMKDELIETESEFVDGF : 110

MPVDLELVAKQNPNVKMGGRYAPRDCVSPHKVAIIIPFRNRQEHLKYWLYYLHPVLQRQ : 204
QPVNLEEVASTNPEVREGGRFAPKDCKALQKVAIIIPFRNREEHLKYWLYYMHPILQRQ : 168
SPMPLERVQRENPGVLMGGRYTPPDCTPAQTVAVIIPFRHREHHLRYWLHYLHPILRRQ : 172
SPMSMERVQRENPDVSLGGKYTPPDCLPRQKVAILIPFRHREHHLKYWLHYLHPILRRQ : 173
PVPSLAEIVERNPRVEPGGRYRPAGCEPRSRTAIIVPHRAREHHLRLLLYHLHPFLQRQ : 152
S-STYHELAAMFPDVQDGGHYTPRMCTPAEKTAIIIPYRNRCRHLYTLLPNLIPMLMRQ : 217

PMNDHNAYRCFSQ-PRHISVAMDKFGFSLPYVQYFGGVSALSKQQFLTINGFPNNYWGW : 312
PMDDRNTYKCYSQ-PRHLSVSMDKFGFRLPYNQYFGGVSALSKEQFTKINGFPNNYWGW : 273
PMDDRNLYRCGDQ-PRHFAIAMDKFGFRLPYAGYFGGVSGLSKAQFLRINGFPNEYWGW : 278
PMDDRNLYRCYEQ-PRHFAVGMDKFGFRLPYAGYFGGVSGLSKSQFLKINGFPNEYWGW : 279
PENDHNLYVCDPRGPRHVAVAMNKFGYSLPYPQYFGGVSALTPDQYLKMNGFPNEYWGW : 258
PIDDRNMYRCNKMGPVHFSPGVNKFKYKLFYSGLFGGVVGFTREQFRLINGASNLYFGW : 323

DKKNE-----------PN------------------------PQRFDRIAHTKETMLSD : 371
DRKNE-----------PN------------------------PERFDRIAHTRETMSSD : 332
DKHNE-----------PN------------------------PQRFTKIQNTKLTMKRD : 337
DKHNE-----------PN------------------------PQRFTKIQNTKMTMKRD : 338
DKGNE-----------EN------------------------PHRFDLLVRTQNSWTQD : 317
DMLNKALGVQAGWNVHPNSKWPLRLFDSVNHAPAEGAGWNVNPDRFKIYSTSRQRQHVD : 433

-----PS                                                     : 400
-----PGS                                                    : 362
-----PPSWPP----------RG                                     : 372
-----PPPRLA----------RG                                     : 373
MLQRRPPARPGPLSTANHTALRGSH                                   : 393
---SIPEDLRIG-PEADNTYLTGNFTIIS                               : 490
```

EXON 1

*Sense* EBER151: 5'-CAGCAGCCGGATGCCCGG-3' (SEQ. ID NO. 17)

*Anti-sense* EBER143: 5'-CCCACAGGCAGGCCATAC-3' (SEQ. ID NO. 18)

EXON 2

*Sense* EBER142: 5'-GATTCCTGACACTGTCCTGTC-3' (SEQ. ID NO. 19)

*Anti-sense* EBER144: 5' CCAACAGGCACATGGACC-3' (SEQ. ID NO. 20)

EXON 3

*Sense* EBER145: 5'-GGAGAGTGGCAAAAGGGCAGG-3' (SEQ. ID NO. 21)

*Anti-sense* EBER146: 5'-GGCTGGGTCCAGCTGAGAAGA-3' (SEQ. ID NO. 22)

EXON 4

*Sense* EBER147: 5'-GGACCCTTACTGACACCTGC-3' (SEQ. ID NO. 23)

*Anti-sense* EBER148: 5'-CCCCACCGCGTGCTTAC-3' (SEQ. ID NO. 24)

EXON 5

*Sense* EBER 149: 5'-CCTGGAGCCTGTTCCAGTCTG-3' (SEQ. ID NO. 25)

*Anti-sense* EBER150: 5'-GAAGTTGCCTCTGGGGAG-3' (SEQ. ID NO. 26)

EXON 6

*Sense* EBER 132: 5' GTGGACCATTTCCATCCTATC-3' (SEQ. ID NO. 27)

*Anti-sense* 1003pri2: 5' ATGGATCCGAAAACAGAGCCCAGTCTCAG-3' (SEQ. ID NO. 28)

UDP-GALACTOSE: β-*N*-ACETYL-GLUCOSAMINE β-1,4-GALACTOSYL-TRANSFERASE, β4GAL-T2

TECHNICAL FIELD

The present invention relates generally to the biosynthesis of glycans found as free oligosaccharides or covalently bound to proteins and glycosphingolipids. This invention is more particularly related to a family of nucleic acids encoding UDP-D-galactose: β-N-acetylglucosamine β-1,4-galactosyltransferases (β4Gal-transferases), which add galactose to the hydroxy group at carbon 4 of 2-acetamido-2-deoxy-D-glucose (GlcNAc). This invention is more particularly related to a gene encoding the second member of the family of β4Gal-transferases, termed β4Gal-T2, probes to the DNA encoding β4Gal-T2, DNA constructs comprising DNA encoding β4Gal-T2, recombinant plasmids and recombinant methods for producing β4Gal-T2, recombinant methods for stably transfecting cells for expression of β4Gal-T2, and methods for identification of DNA polymorphism in patients.

BACKGROUND OF THE INVENTION

The UDP-galactose: β-N-acetyl-glucosamine β-1,4-galactosyltransferase (β4Gal-T1) was the first animal glycosyltransferase to be isolated and cloned (Narimatsu et al., 1986; Shaper et al., 1986; Nakazawa et al, 1988; Shaper et al., 1988; D'Agostaro et al., 1989), and early searches for homologous genes by low stringency Southern hybridisation suggested that this gene was unique. Characterisation of β4Gal-transferase activities from different sources, however, indicate that distinct activities exist (Sheares and Carlson, 1984; Furukawa et al., 1990). Emerging evidence now reveal that several β4galactosyltransferase genes may exist. Shaper and colleagues (Shaper et al., 1995) have identified two different chick cDNA sequences, which have 65% and 48% sequence similarity to human β4Gal-T1. Both chick cDNAs were shown to encode catalytically active p4Gal-transferases (Shaper et al., 1997). Two independent groups have analysed β4Gal-transferase activities in mice homozygously deficient for β4Gal-T1 (Asano et al., 1997; Lu et al., 1997). Both studies showed residual β4Gal-transferase activity, providing clear evidence for the existence of additional β4Gal-transferases. Thus, the β4Gal-T1 gene is likely to be part of a homologous gene family with recognisable sequence motifs, and this is supported by a large number of human ESTs with sequence similarities to β4Gal-T1 in EST databases (National Center for Biotechnology Information).

β-1,4-Galactosyltransferase activities add galactose to different acceptor substrates including free oligosaccharides, N- and O-linked glycoproteins, and glycosphingolipids (Kobata, 1992). In addition, β4Gal-T1 is modulated by α-lactalbumin to function as lactose synthase and hence has a major role in lactation (Brew et al., 1968). Given the diverse functions of β-1,4-galactosyltransferase activities and the evidence that multiple β4Gal-transferases exist, it is likely that these enzymes may have different kinetic properties. Furukawa et al (Furukawa et al., 1990) showed that liver β4Gal-transferase activity was near 20-fold higher with asialo-agalacto-transferrin compared to asialo-agalacto-IgG, whereas the activity found in T and B cells only showed a 4 to 5-fold difference with the two substrates. The β4Gal-transferase activity in B cells of rheumatoid arthritis patients appear to be similar to B cells from healthy controls with several substrates including asialo-agalacto-transferrin (Furukawa et al., 1990) and βGlcNAc-pITC-BSA (Keusch et al., 1995), but different with asialo-agalacto-IgG (Furukawa et al., 1990). Furthermore, the Km for UDP-Gal of β4Gal-transferase activity from B cells of rheumatoid arthritis patients were 2-fold higher (35.6 mM) than normal B cells (17.6 mM) (Furukawa et al., 1990). Finally, the activity in B cells for asialo-agalacto-transferrin was more sensitive to α-lactalbumin inhibition than the activity with asialo-agalacto-IgG. A number of studies have concluded that there was no change in β4Gal-transferase activity in B cells of rheumatoid arthritis patients (Wilson et al., 1993; Axford et al., 1994). However, if multiple β4Gal-transferases exist, it is possible that the contradictory findings of Furukawa et al. (Furukawa et al., 1990) can be explained by a model with two β4Gal-transferases with different kinetic parameters expressed in normal B cells, and a selective down regulation of one in B cells of rheumatoid arthritis patients.

Access to additional existing β4Gal-transferase genes encoding β4Gal-transferases with better kinetic properties than β4Gal-T1 would allow production of more efficient enzymes for use in galactosylation of oligosaccharides, glycoproteins, and glycosphingolipids. Such enzymes could be used, for example, in pharmaceutical or other commercial applications that require synthetic galactosylation of these or other substrates that are not or poorly acted upon by β4Gal-T1, in order to produce appropriately glycosylated glycoconjugates having particular enzymatic, immunogenic, or other biological and/or physical properties.

Consequently, there exists a need in the art for additional UDP-galactose: β-N-acetyl-glucosamine β-1,4-galactosyltransferases and the primary structure of the genes encoding these enzymes. The present invention meets this need, and further presents other related advantages.

SUMMARY OF THE INVENTION

The present invention provides isolated nucleic acids encoding human UDP-galactose: β-N-ace-tylglucosamine β1,4-galactosyltransferase (β4Gal-T2), including cDNA and genomic DNA. β4Gal-T2 has better kinetic parameters than β4Gal-T1, as exemplified by its lower Km for UDP-Gal and its better activity with saccharide derivatives, glycoprotein substrates, and βGlcNAc-glycopeptides. The complete nucleotide sequence of β4Gal-T2, SEQ ID NO:1, is set forth in FIG. 2.

In one aspect, the invention encompasses isolated nucleic acids comprising the nucleotide sequence of nucleotides 1–1116 as set forth in SEQ ID NO:1 or sequence-conservative or function-conservative variants thereof Also provided are isolated nucleic acids hybridizable with nucleic acids having the sequence of SEQ ID NO:1 or fragments thereof or sequence-conservative or function-conservative variants thereof; preferably, the nucleic acids are hybridizable with β4Gal-T2 sequences under conditions of intermediate stringency, and, most preferably, under conditions of high stringency. In one embodiment, the DNA sequence encodes the amino acid sequence, SEQ ID NO:2, also shown in FIG. 2, from methionine (amino acid no. 1) to glycine (amino acid no. 372). In another embodiment, the DNA sequence encodes an amino acid sequence comprising a sequence from tyrosine (no. 31) to glycine (no. 372) of SEQ ID NO:3.

In a related aspect, the invention provides nucleic acid vectors comprising β4Gal-T2 DNA sequences, including but not limited to those vectors in which the β4Gal-T2 DNA sequence is operably linked to a transcriptional regulatory element, with or without a polyadenylation sequence. Cells comprising these vectors are also provided, including without limitation transiently and stably expressing cells. Viruses, including bacteriophages, comprising β4Gal-T2-derived DNA sequences are also provided. The invention also encompasses methods for producing β4Gal-T2 polypeptides. Cell-based methods include without limitation those comprising: introducing into a host cell an isolated DNA molecule encoding β4Gal-T2, or a DNA construct comprising a DNA sequence encoding β4Gal-T2; growing the host cell under conditions suitable for β4Gal-T2 expression; and isolating β4Gal-T2 produced by the host cell. A method for generating a host cell with de novo stable expression of β4Gal-T2 comprises: introducing into a host cell an isolated DNA molecule encoding β4Gal-T2 or an enzymatically active fragment thereof (such as, for example, a polypeptide comprising amino acids 31–372 of SEQ ID NO:2), or a DNA construct comprising a DNA sequence encoding β4Gal-T2 or an enzymatically active fragment thereof, selecting and growing host cells in an appropriate medium; and identifying stably transfected cells expressing β4Gal-T2. The stably transfected cells may be used for the production of β4Gal-T2 enzyme for use as a catalyst and for recombinant production of peptides or proteins with appropriate galactosylation. For example, eukaryotic cells, whether normal or diseased cells, having their glycosylation pattern modified by stable transfection as above, or components of such cells, may be used to deliver specific glycoforms of glycopeptides and glycoproteins, such as, for example, as inmunogens for vaccination.

In yet another aspect, the invention provides isolated β4Gal-T2 polypeptides, including without limitation polypeptides having the sequence set forth in SEQ ID NO:2, polypeptides having the sequence of amino acids 31–372 as set forth in SEQ ID NO:3, and a fusion polypeptide consisting of at least amino acids 31–372 as set forth in SEQ ID NO:3 fused in frame to a second sequence, which may be any sequence that is compatible with retention of β4Gal-T2 enzymatic activity in the fusion polypeptide. Suitable second sequences include without limitation those comprising an affinity ligand or a reactive group.

In another aspect of the present invention, methods are disclosed for screening for mutations in the coding region (exons I–VII) of the β4Gal-T2 gene using genomic DNA isolated from, e.g., blood cells of patients. In one embodiment, the method comprises: isolation of DNA from a patient, PCR amplification of coding exons I–VII; DNA sequencing of amplified exon DNA fragments and establishing therefrom potential structural defects of the β4Gal-T2gene associated with disease.

These and other aspects of the present invention will become evident upon reference to the following detailed description and drawings.

BRIEF DESCRIPTION OF THE DRAWINGS

FIG. 2 depicts the DNA sequence of the β4Gal-T2, SEQ ID NO:2 (accession #Y12509) gene and the predicted amino acid sequence of β4Gal-T2. The amino acid sequence is shown in single letter code. The hydrophobic segment representing the putative transmembrane domain is double underlined, and adjacent charged amino acids are single-stipple underlined. Potential N-linked glycosylation sites are indicated by an asterisk. The locations of primers used for RT-PCR preparation of the expression construct are indicated by single underlining.

FIGS. 3A and 3B are an illustration of a sequence comparison between human β4Gal-T1 SEQ ID NO:4 (GenBank accession # M22921), human β4Gal-T2, SEQ ID NO:2 human β4Gal-T3, SEQ ID NO:5 (GenBank accession #Y22921), chick gene one, SEQ ID NO:6 (GenBank accession # U19890), chick gene two, SEQ ID NO:7 (GenBank accession #U19889), and a snail β4GlcNAc-transferase, SEQ ID NO:8.

FIG. 9 show sequences of the primers that were used for amplification of all exons.

DETAILED DESCRIPTION OF THE INVENTION

Figure 1:
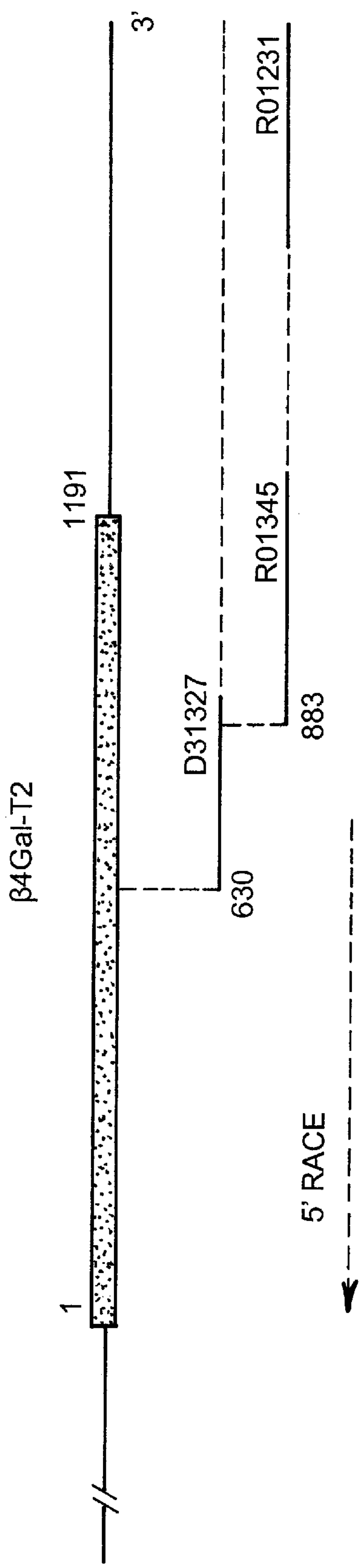
FIG. 1 depicts the strategy for identification and cloning of β4Gal-T2, SEQ ID NO:1. Identified ESTs are indicated by their GenBank accession numbers with available sequence lengths in parenthesis. Vertical stippled lines labelled with numbers indicate 5' positions of EST clones compared to the coding sequence of the gene and coding region, SEQ ID NO:33.

All patent applications, patents, and literature references cited in this specification are hereby incorporated by reference in their entirety. In the case of conflict, the present description, including definitions, is intended to control.

Definitions:

1. "Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases (see below).

2. "Complementary DNA or cDNA" as used herein refers to a DNA molecule or sequence that has been enzymatically synthesized from the sequences present in an mRNA template, or a clone of such a DNA molecule. A "DNA Construct" is a DNA molecule or a clone of such a molecule, either single- or double-stranded, which has been modified to contain segments of DNA that are combined and juxtaposed in a manner that would not otherwise exist in nature. By way of non-limiting example, a cDNA or DNA which has no introns is inserted adjacent to, or within, exogenous DNA sequences.

3. A plasmid or, more generally, a vector, is a DNA construct containing genetic information that may provide for its replication when inserted into a host cell. A plasmid generally contains at least one gene sequence to be expressed in the host cell, as well as sequences that facilitate such gene expression, including promoters and transcription initiation sites. It may be a linear or closed circular molecule.

4. Nucleic acids are "hybridizable" to each other when at least one strand of one nucleic acid can anneal to another nucleic acid under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. Typically, hybridization of two sequences at high stringency (such as, for example, in an aqueous solution of 0.5×SSC, at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C. require correspondingly less overall complementarily between the hybridizing sequences. (1×SSC is 0.15 M NaCl, 0.015 M Na citrate.)

5. An "isolated" nucleic acid or polypeptide as used herein refers to a component that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

6. A "probe" refers to a nucleic acid that forms a hybrid structure with a sequence in a target region due to complementarily of at least one sequence in the probe with a sequence in the target region.

7. A nucleic acid that is "derived from" a designated sequence refers to a nucleic acid sequence that corresponds to a region of the designated sequence. This encompasses sequences that are homologous or complementary to the sequence, as well as "sequence-conservative variants" and "function-conservative variants". Sequence-conservative variants are those in which a change of one or more nucleotides in a given codon position results in no alteration in the amino acid encoded at that position. Function-conservative variants of β4Gal-T2 are those in which a given amino acid residue in the polypeptide has been changed without altering the overall conformation and enzymatic activity (including substrate specificity) of the native polypeptide; these changes include, but are not limited to, replacement of an amino acid with one having similar physico-chemical properties (such as, for example, acidic, basic, hydrophobic, and the like).

8. A "donor substrate" is a molecule recognized by, e.g., a galactosyltransferase and that contributes a galactosyl moiety for the transferase reaction. For β4Gal-T2, a donor substrate is UDP-galactose. An "acceptor substrate" is a molecule, preferably a saccharide or oligosaccharide, that is recognized by, e.g., a galatosyltransferase and that is the target for the modification catalyzed by the transferase, i.e., receives the galatosyl moiety. For β4Gal-T2, acceptor substrates include without limitation oligosaccharides, glycoproteins, O-linked GlcNAc-glycopeptides, and glycosphingolipids containing the sequences GlcNAcβ1-3Gal, GlcNAcβ1-6Gal, GlcNAcβ1-6GalNAc, GlcNAcβ1-3GalNAc, GlcNAcβ1-2Man, GlcNAcβ1-4Man, GlcNAcβ1-6Man, GlcNAcβ1-3 Man, Glcβ1-ceramide.

The present invention provides the isolated DNA molecules, including genomic DNA and cDNA, encoding the UDP-galactose: β-N-acetylglucosamine β-1,4-galactosyltransferase (β4Gal-T2).

β4Gal-T2 was identified by analysis of EST database sequence information, and cloned based on EST and 5'RACE cDNA clones. The cloning strategy may be briefly summarized as follows: 1) synthesis of oligonucleotides derived from EST sequence information, designated EBER102, SEQ ID NO:30 and EBER 104, SEQ ID NO:31; 2) successive 5'-rapid amplification of cDNA ends (5'RACE) using commercial Marathon-Ready cDNA; 3) cloning and sequencing of 5'RACE cDNA; 4) identification of a novel cDNA sequence corresponding to β4Gal-T2; 5) construction of expression constructs by reverse-transcription-polymerase chain reaction (RT-PCR) using Colo205 human cell line mRNA; 6) expression of the cDNA encoding β4Gal-T2 in Sf9 (*Spodoptera frugiperda*) cells. More specifically, the isolation of a representative DNA molecule encoding a novel second member of the mammalian UDP-galactose: β-N-acetylglucosamine β-1,4-galactosyltransferase family involved the following procedures described below.

Identification of DNA Homologous to β4Gal-T1.

Novel human DNA sequences with apparent homology to the human β4Gal-T1 gene (Masri et al., 1988) were identified by sequence similarity searches of the dbEST database at The National Center for Biotechnology Information, USA, using the BLASTn and tBLASTn algorithms. Composites for identified novel genes were compiled and analysed for sequence similarity to human β4Gal-T1. EST cDNA clones with the longest inserts (FIG. 1) were obtained from Genome Systems Inc, USA.

Cloning of human B4Gal-T2.

Two partly overlapping ESTs with predicted sequence similarity to β4Gal-T1 were identified (FIG. 1). Sequencing of the inserts revealed an open reading frame which potentially encoded a sequence similar to β4Gal-T1, but the 5' sequence was shorter and without an initiation codon. Further 5' sequence was obtained by 5' RACE using human fetal brain Marathon-Ready cDNA (Clontech) in combination with anti-sense primers EBER102 and EBER104. The 5'RACE products were cloned and multiple clones were sequenced. The entire sequence was confirmed by sequencing genomic P1 clones. The composite sequence contained an open reading frame of 1116 bp (FIG. 2), with an overall sequence identity of approximately 63% to β4Gal-T1. The predicted open reading frame has one potential initiation codon in agreement with Kozak's rule (Kozak, 1992). The predicted coding sequence depicts a type II transmembrane glycoprotein with a 11 amino acid residue N-terminal cytoplasmic domain, a transmembrane segment of 21 residues, and a stem region and catalytic domain of 340 residues, with three potential N-linked glycosylation sites (FIG. 2). Multiple alignment analysis (ClustalW) of human β4Gal-T1 (accession #M22921), human β4Gal-T2, and human β4Gal-T3 (accession #Y12510) presented in FIGS. 3A and 3B demonstrated sequence significant similarities especially in the central and C-terminal region and conservation of cysteine residues. The N-terminal regions show no sequence similarity. A 3' untranslated region without polyadenylation signals was included in the oligo-dT primed EST cDNA clones sequenced. The 3' ESTs (STsG4681) were linked to chromosome 1 between D1S2861 and D1S211 microsatellite markers at 73–75 cM (NCBI).

Expression of β4Gal-T2.

An expression construct designed to encode amino acid residues 31–372 of β4Gal-T2, SEQ ID NO:3, was prepared by RT-PCR with mRNA from Colo205 cell line, using the primer pair EBER100FOR, SEQ ID NO:9 and EBER114, SEQ ID NO:10 10(FIG. 2). Expression of a soluble construct of β4Gal-T2 in Sf9 cells (Pharmingen) resulted in marked increase in galactosyltransferase activity using the βGlcNAc-benzyl acceptor substrate compared to uninfected cells or cells infected with control constructs for polypeptide GalNAc-transferases or histo-blood group A and O genes (Bennett et al., 1996; Gentzsch and Tanner, 1996) (Table I).

TABLE I

Substrate specificity of β4Gal-transferases

| Substrate concentration | β4Gal-T2[a] (nmol/min/ml) 1 mM | 3 mM | 9 mM |
|---|---|---|---|
| D-GlcNAc | 1.4 | 3.2 | 4.8 |
| Bz-β-D-GlcNAc | 6.8 | 3.6 | 1.5 |
| Bz-α-D-GlcNAc | 0.4 | 1.1 | 1.7 |
| o-Nph-α-D-GlcNAc | 0.4 | 0.8 | 1.5 |
| p-Nph-β-D-GlcNAc | 3.0 | 2.3 | 0.9 |
| p-Nph-1-thio-β-D-GlcNAc | 1.2 | 1.6 | 0.2 |
| 4-Me-lumb-β-D-GlcNAc | 0.8 | 0.6 | 0.4 |
| β-D-GlcNAc-(1-3)-β-D-Gal-1-OMe | 5.8 | 7.7 | ND[b] |
| β-D-GlcNAc-(1-6)-α -D-Man-1-OMe | 8.5 | 11.3 | ND |
| Bz-2-(2-β-D-GlcNAc)-α-D-GlcNAc | 9.9 | 2.6 | 1.3 |
| 4-Me-lumb-β-D-GalNAc | ND | 0.0 | ND |
| o-Nph-β-D-GalNAc- | ND | 0.0 | ND |
| Bz-α-D-GalNAc | ND | 0.0 | ND |
| 4-Me-lumb-β-D-Gal | ND | 0.0 | ND |
| o-Nph-β-D-Gal | ND | 0.0 | ND |

Figure 4A:
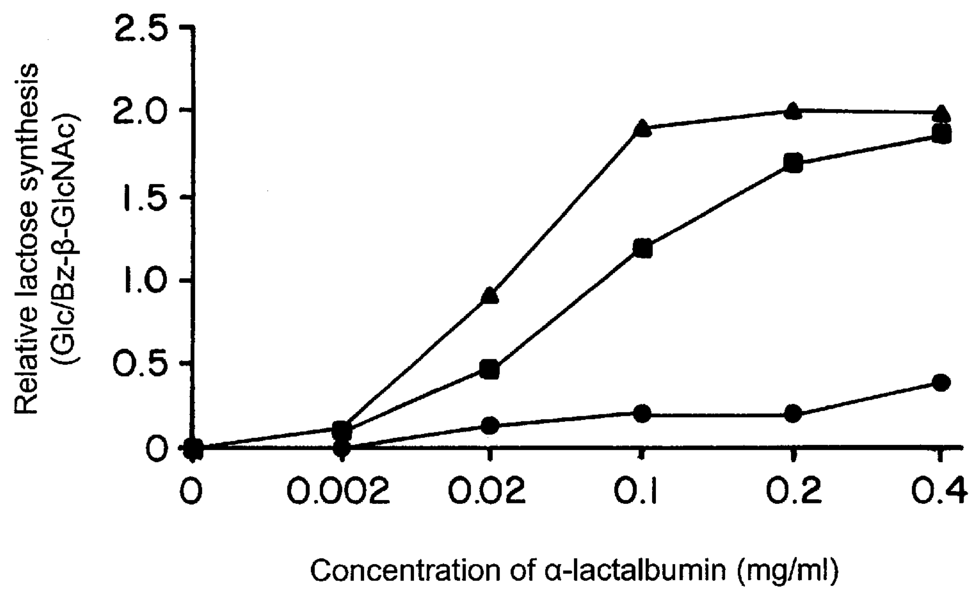
FIGS. 4A and 4B depict α-lactalbumin modulation of β4galactosyltransferase activities. 4A: Activities with glucose in the presence of increasing amounts of α-lactalbumin. The results are presented relative to the activities obtained with 40 mM glucose. 4B: Activities with GlcNAc in the presence of increasing amounts of α-lactalbumin. The results are presented relative to the activities obtained with 2 mM (for bovine milk enzyme and β4Gal-T3) or 0.25 mM βGlcNAc-benzyl (for β4Gal-T2). Purified bovine milk enzyme or media from Sf9 cells expressing secreted forms of either β4Gal-T2 or -T3 were used as enzyme sources. Designations: ▲Bovine milk Gal-transferase mainly representing β4Gal-T1; ■β4Gal-T2; ●β4Gal-T3.
Figure 4B:
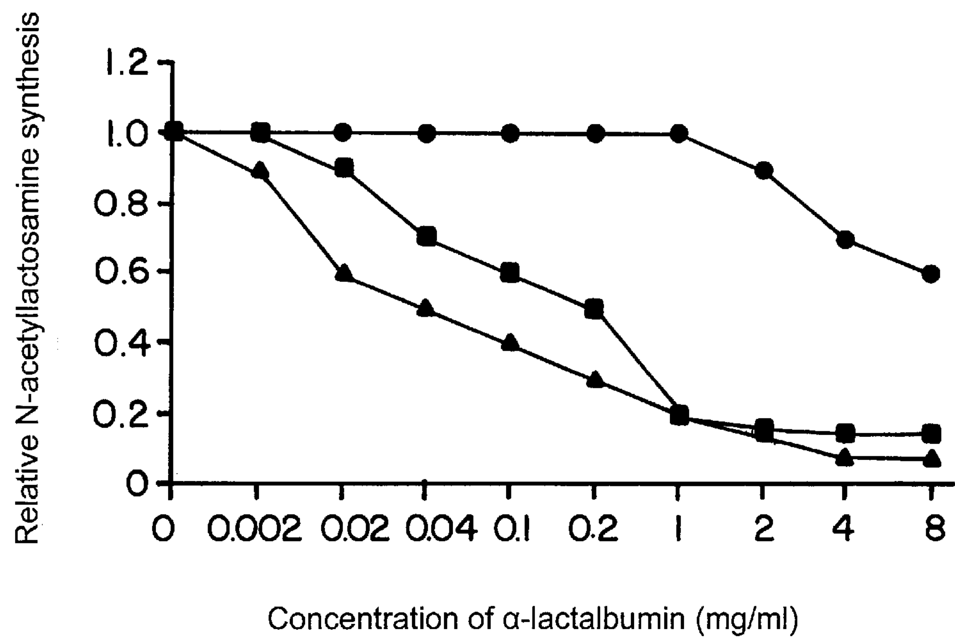
Figure 5A:
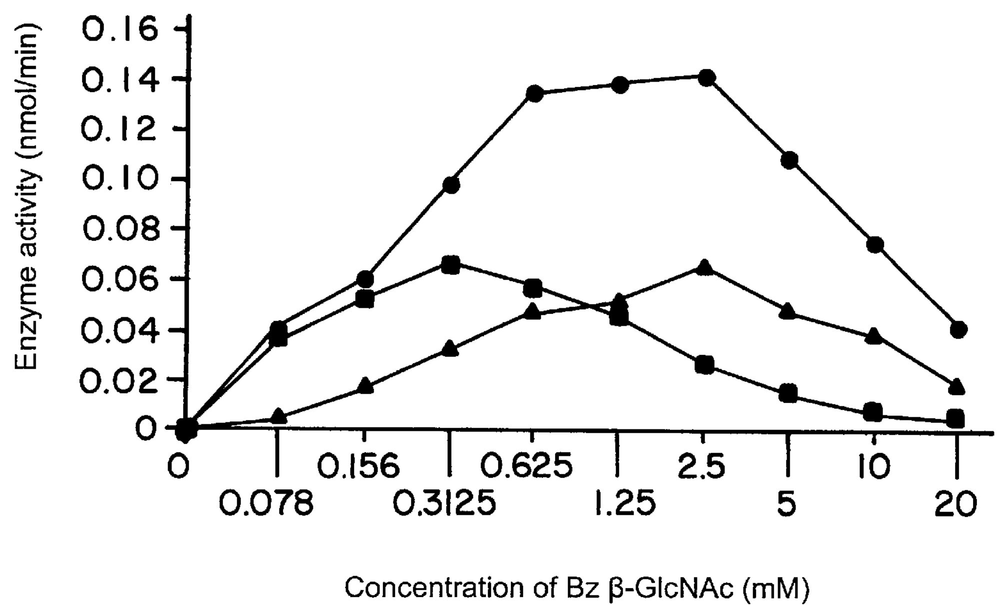
FIGS. 5A and 5B depicts differential inhibition of β4Gal-transferase activities by high acceptor substrate concentrations. 5A: βGlcNAc-benzyl. 5B: GlcNAc. Designations as in FIGS. 4A and 4B.
Figure 5B:
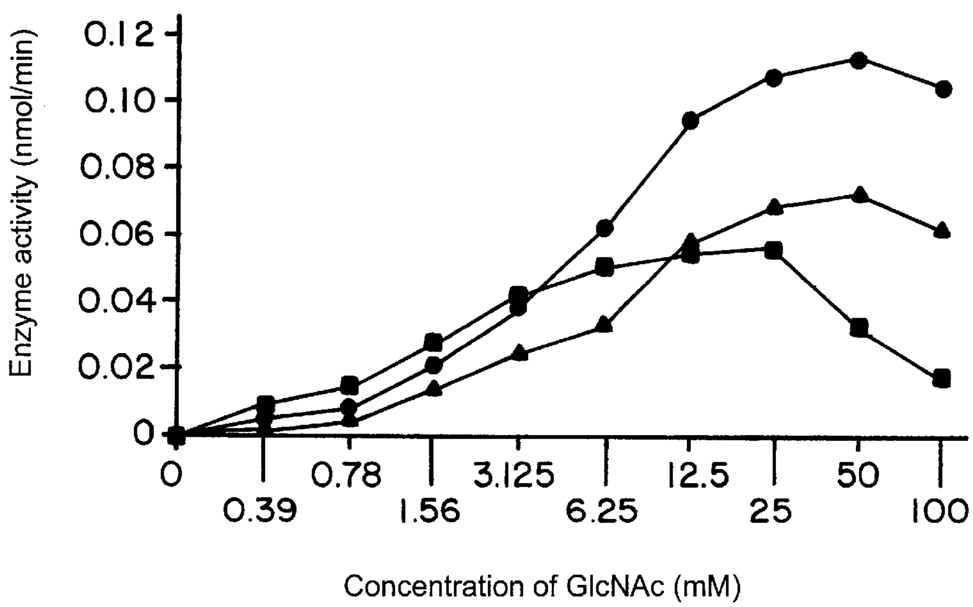

[a]Enzyme sources were media of infected Sf9 cells. Background values obtained with uninfected cells or cells infected with an irrelevant construct were subtracted. The background rates were not higher than 0.5 nmol/min/ml.
[b]ND, not determined Analysis of the substrate specificity of the soluble β4Gal-T2 activity showed that only 13GlcNAc-benzyl and not αGlcNAc-benzyl or αGalNAc-benzyl was an acceptor substrate. Free glucose was not an acceptor, but in the presence of increasing concentrations of α-lactalbumin incorporation rates similar to bovine milk β4Gal-transferase was observed (FIG. 4A). Differences in the concentration of α-lactalbumin to achieve maximum activity with Glc were observed with 0.4 mg/ml required for β4Gal-T2 and only 0.1 mg/ml for the bovine milk enzyme. The activities of both β4Gal-T2 and the bovine milk enzyme with GlcNAc were inhibited by α-lactalbumin, but β4Gal-T1 (bovine milk transferase preparation) was overall more sensitive to inhibition (FIG. 4B). The apparent Km for benzyl-βGlcNAc was 0.16 mM, and the Km for UDP-Gal using benzyl-βGlcNAc was 0.011 mM. The bovine milk β4-galactosyltransferase showed higher Km for UDP-Gal in agreement with previous studies (Fujita-Yamaguchi and Yoshida, 1981; Paquet and Moscarello, 1984; Furukawa et al., 1990; Nakazawa et al., 1991; Malissard et al., 1996), and the measured Km for GlcNAc was similar to that determined in some studies (Powell and Brew, 1974; Moscarello et al., 1985), but 5–10 fold higher than compared to other studies (Fujita-Yamaguchi and Yoshida, 1981; Paquet and Moscarello, 1984; Nakazawa et al., 1991; Malissard et al, 1996). As shown in FIGS. 5A and 5B β4Gal-T2 was inhibited at high concentrations of both benzyl-βGlcNAc and free N-acetylglucosamine to higher degree than bovine milk β4Gal-transferase and β4Gal-T3 (Shur, 1982). β4Gal-T2 showed strict donor substrate specificity for UDP-Gal and did not utilise UDP-GalNAc or UDP-GlcNAc with the acceptor substrates tested. β4Gal-T2 utilised the $Lc_3Cer$ glycosphingolipid substrates, and the product formed with this substrate was confirmed by $^1$H-NMR to be $nLc_3Cer$ similar to what was found for the activity of 4Gal-T3 (Almeida et al., 1997). β4Gal-T2 exhibited the overall best activities with the glycoprotein acceptors ovalbumin, asialo-agalacto-fetuin, and asialo-agalacto-transferrin (Table II).

TABLE II

Substrate specificity of β4-galactosyltransferases with glycopeptide and glycoprotein acceptors

| Acceptor substrate [a] | β4Gal-T2 nmol/min/ml | β4Gal-T3 nmol/min/ml | Bovine milk β4Gal-T nmol/min/μg |
|---|---|---|---|
| β-D-GlcNAc-1-Bz | 3.5 | 3.9 | 3.4 |
| β-D-GlcNAc-1-(FAPGSYPAL) | 1.3 | 0.9 | 1.0 |
| α-D-GalNAc-1-(FAPSNYPAL) | 0.0 | 0.0 | 0.0 |
| Hen egg albumin | 2.0 | 1.0 | 0.7 |
| Asialo-agalacto-Fetuin | 2.8 | 0.7 | 0.8 |
| Asialo-Fetuin | 0.2 | 0.0 | 0.1 |

[a] β-D-GlcNAc-1-Bz was used at 0.25 mM with β4Gal-T2, 0.625 mM with bovine milk β4Gal-T, 2 mM with β4Gal-T3, and 20 mM with β4Gal-T5; glycopeptides were used at 0.1 mM; glycoproteins were used at 10 mg/ml.

The activities of the β4Gal-transferases were analysed relative to benzyl-β-GlcNAc, and β4Gal-T2 showed 2–3 fold higher activity than other β4Gal-transferases tested. β4Gal-T2 also showed the best activity with a synthetic O-linked βGlcNAc-glycopeptide (Table II), suggesting that this enzyme will show higher sensitivity in labeling O-linked βGlcNAc-glycoproteins as well.

Northern Blot Analysis of Human Organs.

Figure 6:
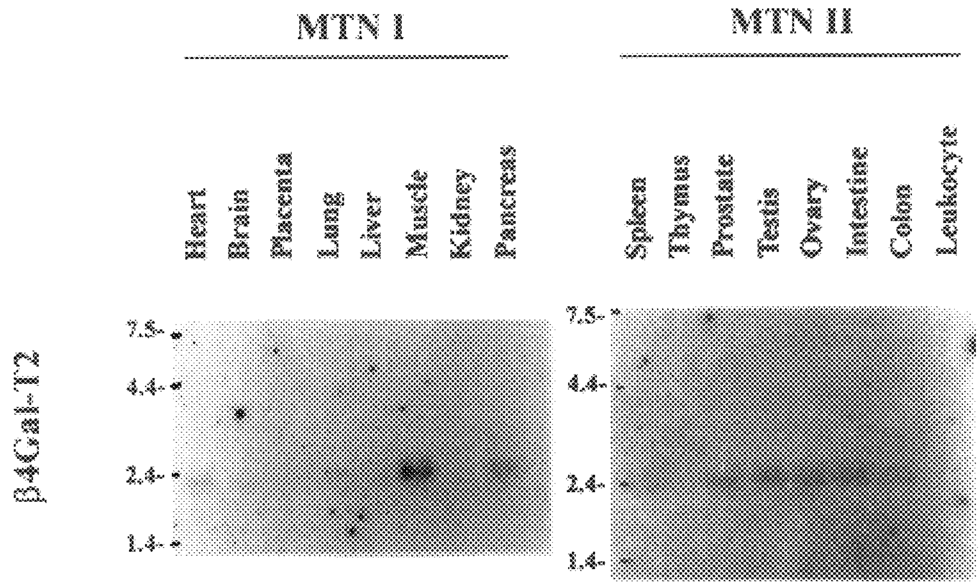
FIG. 6 is a photographic illustration of Northern blot analysis of the expression patterns of β4Gal-T2 in different tissues. MTN signifies Multiple Tissue Northern blots (Clontech).

Northern analysis with mRNA from 16 human adult organs showed a single transcript of both genes of approximately 2.2 kb (FIG. 6). β4Gal-T2 was expressed weakly in several adult organs with highest expression in prostate, testis, ovary, intestine, and muscle.

Genomic Organization of β4Gal-T2 Gene.

Figure 7:
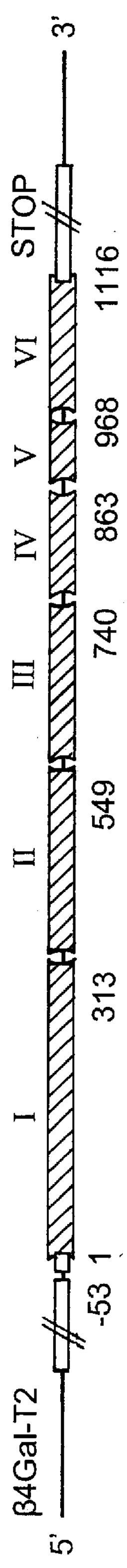
FIG. 7 is a schematic representation of the genomic structure of the coding region of the human β4Gal-T2 gene. The six identified introns are indicated with the nucleotide positions of the 3' exon boundaries. The coding region is placed in 6 exons designated I–VI.
Figure 8:
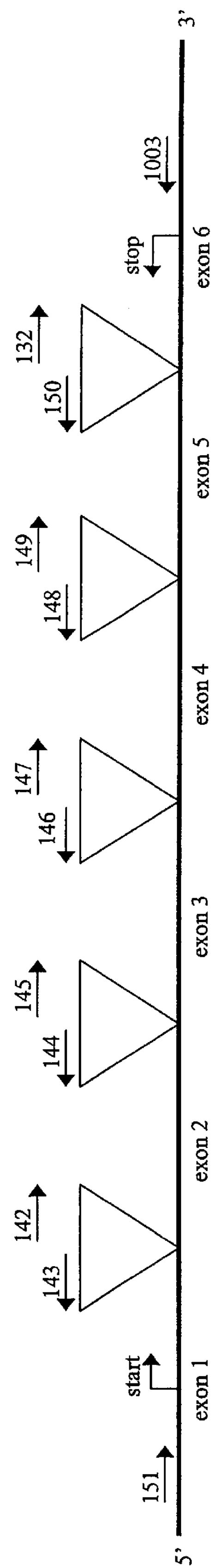
FIG. 8 is a schematic representation of forward and reverse PCR primers that can be used to amplify different regions of the β4Gal-T2.

The present invention also provides isolated genomic DNA molecules encoding β4Gal-T2. A human P1 library (DuPont Merck Pharmaceutical Company Human Foreskin Fibroblast P1 Library) was screened using primer pairs EBER100, SEQ ID NO:29, and EBER102, SEQ ID NO:30. Three clones; DPMC-HFF#10638:515:G9, DPMC-HFF#10639:516:G4, and DPMC-HFF#10640:924:A11, were obtained from Genome Systems. Southern blot analysis with various oligonucleotides covering the 3' and 5' coding sequence of the existing full length β4Gal-T2 cDNA indicated that the entire coding sequence was included in the P1 clone. A comparative Southern blot analysis between cloned P1 DNA and total human genomic DNA using a full length cDNA as probe gave similar patterns, validating the use of cloned P1 DNA as a model. The coding region of β4Gal-T2 were found in six exons (FIG. 7). The nucleic acid sequences for these exons numbered as exons I, II, III, IV, V and VI are depicted as SEQ ID NOS:11–16 respectively. Human and mouse β4Gal-T1 is encoded in six exons (Hollis et al., 1989; Mengle-Gaw et al., 1991). Comparison of the intron/exon boundaries of β4Gal-T1, -T2, and -T3, revealed that the five introns in the coding regions of the three genes are placed identically. FIGS. 8 and 9 depict a PCR strategy and primer sequences for amplification of all coding exons in β4Gal-T2 using genomic DNA. The primer sequences for cloning each exon are depicted in FIG. 9 and defined as EBER151 and EBER143 for Exon I, SEQ ID NOS:17 and 18, respectively; EBER142 and EBER144 for Exon II, SEQ ID NOS:19 and 20, respectively; EBER145 and EBER146 for Exon III, SEQ ID NOS:21 and 22, respectively; EBER147 and EBER148 for Exon IV, SEQ ID NOS:23 and 23, respectively; EBER149 and EBER150 for Exon V, SEQ ID NOS:25 and 26, respectively; and EBER132 and 1003pri2 for Exon VI, SEQ ID NOS:27 and 28, respectively.

DNA, Vectors, and Host Cells

In practicing the present invention, many conventional techniques in molecular biology, microbiology, recombinant DNA, and immunology, are used. Such techniques are well known and are explained fully in, for example, Sambrook et al., 1989*, Molecular Cloning: A Laboratory Manual*, Second Edition, Cold Spring Harbor Laboratory Press, Cold Spring Harbor, N.Y., *DNA Cloning: A Practical Approach*, Volumes I and II, 1985 (D. N. Glover ed.); *Oligonucleotide Synthesis*, 1984, (M. L. Gait ed.); *Nucleic Acid Hybridization*, 1985, (Hames and Higgins), *Transcription and Translation*, 1984 (Hames and Higgins eds.); *Animal Cell Culture*, 1986 (R. I. Freshney ed ), *Immobilized Cells and Enzymes*, 1986 (IRL Press); Perbal, 1984*, A Practical Guide to Molecular Cloning*; the sectors, *Methods in Enzymology* (Academic Press, Inc.), *Gene Transfer Vectors for Mammalian Cells*, 1987 (J. H. Miller and M. P. Calos eds., Cold Spring Harbor Laboratory), *Methods in Enzymology* Vol. 154 and Vol. 155 (Wu and Grossman, and Wu, eds., respectively); *Immunochemical Methods in Cell and Molecular Biology*, 1987 (Mayer and Waler, eds; Academic Press, London), Scopes, 1987*, Protein Purification: Principles and Practice*, Second Edition (Springer-Verlag, N.Y.) and Handbook of *Experimental Immunology*, 1986, Volumes I–IV (Weir and Blackwell eds.).

The invention encompasses isolated nucleic acid fragments comprising all or part of the nucleic acid sequence disclosed herein as SEQ ID NO:1. The fragments are at least about 8 nucleotides in length, preferably at least about 12 nucleotides in length, and most preferably at least about 15–20 nucleotides in length. The invention further encompasses isolated nucleic acids comprising sequences that are hybridizable under stringency conditions of 2×SSC, 55° C., to SEQ ID NO:1; preferably, the nucleic acids are hybridizable at 2×SSC, 65° C.; and most preferably, are hybridizable at 0.5×SSC, 65° C.

The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural human regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

According to the present invention, useful probes comprise a probe sequence at least eight nucleotides in length that consists of all or part of the sequence from among the sequences designated SEQ ID NO:1 or sequence-conservative or function-conservative variants thereof, or a complement thereof, and that has been labelled as described above.

The invention also provides nucleic acid vectors comprising the disclosed sequence or derivatives or fragments thereof A large number of vectors, including plasmid and fungal vectors, have been described for replication and/or expression in a variety of eukaryotic and prokaryotic hosts, and may be used for gene therapy as well as for simple cloning or protein expression.

Recombinant cloning vectors will often include one or more replication systems for cloning or expression, one or more markers for selection in the host, e.g. antibiotic resistance, and one or more expression cassettes. The inserted coding sequences may be synthesized by standard methods, isolated from natural sources, or prepared as hybrids, etc. Ligation of the coding sequences to transcriptional regulatory elements and/or to other amino acid coding sequences may be achieved by known methods. Suitable host cells may be transformed/transfected/infected as appropriate by any suitable method including electroporation, $CaCl_2$ mediated DNA uptake, fungal infection, microinjection, microprojectile, or other established methods.

Appropriate host cells included bacteria, archebacteria, fungi, especially yeast, and plant and animal cells, especially mammalian cells. Of particular interest are *Saccharomyces cerevisiae, Schizosaccharonlyces pombi*, SF9 cells, C129 cells, 293 cells, *Neurospora*, and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced β4Gal-T2 derived peptides and polypeptides.

Advantageously, vectors may also include a transcription regulatory element (i.e., a promoter) operably linked to the β4Gal-T2-coding portion. The promoter may optionally contain operator portions and/or ribosome binding sites. Non-limiting examples of bacterial promoters compatible with *E. coli* include: â-lactamase (penicillinase) promoter; lactose promoter; tryptophan (trp) promoter; arabinose BAD operon promoter; lambda-derived $P_1$ promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3 phosphate dehydrogenase (GAPDH) promoter, galactokinase (GALI) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences and enhancer sequences which increase expression may also be included; sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are known in the art.

Nucleic acids encoding wild-type or variant polypeptides may also be introduced into cells by recombination events. For example, such a sequence can be introduced into a cell, and thereby effect homologous recombination at the site of an endogenous gene or a sequence with substantial identity to the gene. Other recombination-based methods such as nonhomologous recombinations or deletion of endogenous genes by homologous recombination may also be used.

The nucleic acids of the present invention find use, for example, as probes for the detection of β4Gal-T2 an other species and as templates for the recombinant production of peptides or polypeptides. These and other embodiments of the present invention are described in more detail below.

Polypeptides and Antibodies

The present invention encompasses isolated peptides and polypeptides encoded by the disclosed genomic sequence. Peptides are preferably at least five residues in length.

Nucleic acids comprising protein-coding sequences can be used to direct the recombinant expression of polypeptides in intact cells or in cell-free translation systems. The known genetic code, tailored if desired for more efficient expression in a given host organism, can be used to synthesize oligonucleotides encoding the desired amino acid sequences. The phosphoramidite solid support method of Matteucci et al., 1981, *J. Am. Chem. Soc.* 103:3185, the method of Yoo et al., 1989, *J. Biol. Chem.* 764:17078, or other well known methods can be used for such synthesis. The resulting oligonucleotides can be inserted into an appropriate vector and expressed in a compatible host organism.

The polypeptides of the present invention, including function-conservative variants of the disclosed sequence, may be isolated from native or from heterologous organisms or cells (including, but not limited to, bacteria, fungi, insect, plant, and mammalian cells) into which a protein-coding sequence has been introduced and expressed. Furthermore, the polypeptides may be part of recombinant fusion proteins.

Methods for polypeptide purification are well-known in the art, including, without limitation, preparative disc-gel elctrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against a protein or against peptides derived therefrom can be used as purification reagents. Other purification methods are possible.

The present invention also encompasses derivatives and homologues of polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine), negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

The present invention encompasses antibodies that specifically recognize immunogenic components derived from β4Gal-T2. Such antibodies can be used as reagents for detection and purification of β4Gal-T2.

β4Gal-T2 specific antibodies according to the present invention include polyclonal and monoclonal antibodies. The antibodies may be elicited in an animal host by immunization with β4Gal-T2 components or may be formed by in vitro immunization of immune cells. The immunogenic components used to elicit the antibodies may be isolated from human cells or produced in recombinant systems. The antibodies may also be produced in recombinant systems programmed with appropriate antibody-encoding DNA. Alternatively, the antibodies may be constructed by biochemical reconstitution of purified heavy and light chains. The antibodies include hybrid antibodies (i.e., containing to sets of heavy chain/light chain combinations, each of which recognizes a different antigen), chimeric antibodies (i.e., in which either the heavy chains, light chains, or both, are fusion proteins), and univalent antibodies (i.e., comprised of a heavy chain/light chain complex bound to the constant region of a second heavy chain). Also included are Fab fragments, including Fab' and $F(ab)_2$ fragments of antibodies. Methods for the production of all of the above types of antibodies and derivatives are well-known in the art. For example, techniques for producing and processing polyclonal antisera are disclosed in Mayer and Walker, 1987, *Immunochemical Methods in Cell and Molecular Biology*, (Academic Press, London).

The antibodies of this invention can be purified by standard methods, including but not limited to preparative disc-gel elctrophoresis, isoelectric focusing, HPLC, reversed-phase HPLC, gel filtration, ion exchange and partition chromatography, and countercurrent distribution. Purification methods for antibodies are disclosed, e.g., in *The Art of Antibody Purification*, 1989, Amicon Division, W. R. Grace & Co. General protein purification methods are described in *Protein Purification: Principles and Practice*, R. K. Scopes, Ed., 1987, Springer-Verlag, New York, N.Y.

Anti-β4Gal-T2 antibodies, whether unlabeled or labeled by standard methods, can be used as the basis for imnmunoassays. The particular label used will depend upon the type of immunoassay used. Examples of labels that can be used include, but are not limited to, radiolabels such as $^{32}p$, $^{125}I$, $^{3}H$ and $^{14}C$; fluorescent labels such as fluorescent and its derivatives, rhodamine and its derivatives, dansyl and umbelliferone; chemilurninescers such as luciferia and 2,3-dihydrophthal-azinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described in, e.g., Chan (Ed.), 1987, *Immunoassay: A Practical Guide*, Academic Press, Inc., Orlando, Fla.

The following examples are intended to further illustrate the invention without limiting its scope.

EXAMPLE 1.

A: Identification of cDNA Homologous to β4Gal-T1 by Analysis of EST Database Sequence Information.

Database searches were performed with the coding sequence of the human β4Gal-T1 sequence (Masri et al., 1988) using the BLASTn and tBLASTn algorithms against the dbEST database at The National Center for Biotechnology Information, USA. The BLASTn algorithm was used to identify ESTs representing the query gene (identities of ≧95%), whereas tBLASTn was used to identify non-identical, but similar EST sequences. ESTs with 50–90% nucleotide sequence identity were regarded as different from the query sequence. The results of tBLASTn searches were evaluated by visual inspection after elimination of ESTs regarded as identical to the query sequence (<95% nucleotide sequence identity). ESTs with several apparent short sequence motifs and cysteine residues arranged with similar spacing were selected for further sequence analysis. Initially, the identified ESTs (5' sequence) were used in BLASTn searches of the dbEST database to search for overlapping ESTs (95–100% identity in at least 30 bp) (FIG. 1). If new ESTs were identified, the procedure was repeated and sequences merged. In addition, all identified ESTs were analysed in the Unigene database in order to confirm that they were from the same gene transcript, and to select cDNA clones with the longest inserts as well as identify additional ESTs with a non-overlapping 5' sequence. Composites of all the sequence information for each set of ESTs were compiled and analysed for sequence similarity to human β4Gal-T1.

B: Cloning and Sequencing of β4Gal-T2.

Two partly overlapping ESTs were identified (FIG. 1). Sequencing of the inserts revealed an open reading frame which potentially encoded a sequence similar to β4Gal-T1, but the 5' sequence was shorter and without an initiation codon. Further 5' sequence was obtained by 5' RACE using human fetal brain Marathon-Ready cDNA (Clontech) in combination with anti-sense primers EBER102 (5'-GAAACTGAGCCTTACTCAGGC), SEQ ID NO:30 , and EBER104 (5'-TCCACATCGCTGAAGATGAAGC), SEQ ID NO:31, for 35 cycles at 95° C., 45 sec. 55° C., 15 sec. 68° C., 3 min, using the Expand kit enzyme (Boehringer Mannheim). The RACE products were cloned into the BamHI site of pT7T3U19 and multiple clones were sequenced. The entire sequence was confirmed by sequencing genomic P1 clones.

EXAMPLE 2

A: Expression of βGal-T2 in Sf9 Cells.

An expression construct designed to encode amino acid residues 31–372 of β4Gal-T2, SEQ ID NO:3, was prepared by RT-PCR with mRNA from Colo205 cell line, using the primer pair EBER100FOR (5'-TACTTTGACGTCTACGCCCAG), SEQ ID NO:9, and EBER114 (5'-GAAAACAGAGCCCAGCTCAG), SEQ ID NO:10, with BamHI restriction sites (FIG. 2). The PCR product were cloned into the BamHI site of pAcGP67 (Pharmingen), and the construct sequenced to verify correct insertion and sequence. The plasmid pAcGP67-β4Gal-T2-sol was co-transfected with Baculo-Gold™ DNA (Pharmigen) as described previously (Bennett et al., 1996). Recombinant Baculo-virus were obtained after two successive amplifications in Sf9 cells grown in serum-containing medium, and titres of virus were estimated by titration in 24-well plates with monitoring of enzyme activities. Controls included pAcGP67-134Gal-T3-sol (Almeida et al., 1997) and pAcGP67-GalNAc-T3-sol (Bennett et al, 1996).

B: Analysis of βGal-2 Activity.

Standard assays were performed in 50 ml total reaction mixtures containing 25 mM Tris (pH 7.5), 10 MN $MnCl_2$, 0.25% Triton X-100, 100 mM UDP-[$^{14}$C]-Gal (2,300 cpm/nmol) (Amersham), and varying concentration of acceptor substrates (Sigma) (see Table I for structures). The soluble constructs were assayed with 5–20 ml of culture supernatant from infected cells, whereas the full length construct was assayed with 1% Triton X-100 homogenates of washed cells. Bovine milk β1,4Gal-transferase (Sigma) was used as control. Assays used for determination of Km of acceptor substrates were modified to include 200 mM UDP-[$^{14}$C]-Gal, and assays for donor substrate Km were performed with 2 mM (for β4Gal-T3 and bovine milk Gal-T) or 0.25 mM βGlcNAc-benzyl.

Reaction products were quantified by Dowex-1 chromatography. Assays with hen egg Ovalbumin (Sigma), asialo-fetuin (Sigma), and asialo-agalacto-fetuin (Sigma, treated with βgalactosidase) were performed with the standard reaction mixture modified to contain 200 mM UDP-Gal, 54 mM NaCl, and 0.5 mg Ovalbumin. The transfer of Gal was evaluated after precipitation by filtration through Whatman GF/C glass fiber filters, C: Stable Expression of Full Coding Sequence of βGal-T2 in CHO Cells.

A cDNA sequence encoding the full coding sequence of the putative β4Gal-T2 gene was derived by RT-PCR using primers EBER 120 (5'-AGCGGATCCATGAGCAGACTGCTGGGG-3'), SEQ ID NO:33 and EBER 114 with BamHI restriction sites introduced. The PCR product was designed to yield a β4Gal-T2 protein with a hydrophobic transmembrane retention signal in order to have the enzyme expressed and positioned in the appropriate Golgi compartment of the transfected cell. The PCR product was inserted into the BamHI site of a mammalian expression vector pCDNA3 (Invitrogen), and the construct, pCDNA3- β4Gal-T2-mem, was transfected into CHO and stable transfectants were selected.

D: Stable Expression of the Soluble Form of βGal-T2 in CHO Cells.

cDNA pAcGP67- β4Gal-T2-sol containing the coding sequence of the putative soluble β4Gal-T2 enzyme was cloned into the BamHI site of a modified mammalian expression vector pCDNA3 (Invitrogen). pcDNA3 had been modified by insertion of an interferon signal peptide sequence into the KpnI/BamHI site of ensuring secretion of the expressed product when cloned into the vector. The pcDNA3-γINF- β4Gal-T2-sol construct was transfected into CHO and stable transfectants were selected.

EXAMPLE 3

Restricted Organ Expression Pattern of βGal-T2

Human Multiple Tissue northern blots were obtained from Clontech. The soluble expression construct of β4Gal- T2 was used as probe. The probe was random primed labelled using $\alpha P^{32}$dCTP (Amersham) and an oligo labelling kit (Pharmacia). The blots were probed 18 hours at 42° C. as previously described (Bennett et al, 1996), and washed 2×10 min at RT with 2×SSC, 1%Na4P202; 2×20 min at 65° C. with 0.2×SSC, 1% SDS, 1% $Na_4P_2O_2$; and once 10 min with 0.2×SSC at RT.

EXAMPLE 4

Genomic Structure of the Coding Region of β4Gal-T2

A human foreskin genomic P1 library (DuPont Merck Pharmaceutical Company Human Foreskin Fibroblast P1 Library) was screened using primer pair EBER100 (5'-TGAAGGAGGATGCCGCCTATGAC), SEQ ID NO:2, EBER102 (5'-GAAACTGAGCCTTACTCAGGC), SEQ ID NO:30, P1 clones were obtained from Genome Systems Inc, and DNA from P1 phages prepared as recommended by Genome Systems Inc. The entire coding sequence of each gene was sequenced in full using automated sequencing (ABI377, Perkin Elmer) with dye terminator chemistry. Intron/exon boundaries were determined by comparison with the cDNA sequences optimising for the gt/ag rule (Breathnach and Chambon, 1981).

EXAMPLE 5

Analysis of DNA Polymorphism of β4Gal-T2 Gene

Primer pairs as described in FIGS. 8 and 9 have been used for PCR amplification of individual coding sequence of the 6 exons,SEQ ID NO:11–16. Each PCR product was subcloned and the sequence of 10 clones containing the appropriate insert was determined assuring that both alleles of each individual are characterized.

From the foregoing it will be evident that, although specific embodiments of the invention have been described herein for purposes of illustration, various modifications may be made without deviating from the spirit and scope of the invention.

REFERENCES

1. Almeida, R., Amado, M., David, L., Levery, S. B., Holmes, E. H., Merkx, G., van Kessel, A. G., Hassan, H., Bennett, E. P., and Clausen, H. (1997) A Family of Human β4-Galactosyltransferases: Cloning and expression of two novel UDP-Galactose: β-N-Acetylglucosamine β1,4-Galactosyltransferases, β4Gal-T2 and β4Gal-T3. *J. Biol. Chem.*, 272, 31979–31992.
2. Asano, M., Furukawa, K., Kido, M., Matsumoto, S., Umesaki, Y., Kochibe, N., and Iwakura, Y. (1997) Growth retardation and early death of β-1,4-galactosyltransferase knockout mice with augmented proliferation and abnormal differentiation of epithelial cells. *EMBO J.*, 16, 1850–1857.
3. Axford, J. S., Alavi, A., Bond, A., and Hay, F. C. (1994) Differential B lymphocyte galactosyltransferase activity in the MRL mouse model of rheumatoid arthritis. *Autoimmunity.*, 17, 157–163.
4. Bennett, E. P., Hassan, H., and Clausen, H. (1996) cDNA cloning and expression of a novel human UDP-N-acetyl-alpha-D-galactosamine. Polypeptide N-acetylgalactosaminyltransferase, GalNAc-t3. *J. Biol. Chem.*, 271, 17006–17012.
5. Breathnach, R. and Chambon, P. (1981) Organization and expression of eucaryotic split genes coding for proteins. *Ann Rev Biochem.*, 50, 349–383.
6. Brew, K., Vanaman, T. C., and Hill, R. L. (1968) The role of alpha-lactalbumin and the A protein in lactose synthetase: a unique mechanism for the control of a biological reaction. *Proc Natl Acad Sci USA.*, 59, 491–497.
7. D'Agostaro, G., Bendiak, B., and Tropak, M. (1989) Cloning of cDNA encoding the membrane-bound form of bovine beta 1,4-galactosyltransferase. *Eur J Biochem.*, 183, 211–217.
8. Fujita-Yamaguchi, Y. and Yoshida, A. (1981) Purification and characterization of human serum galactosyltransferase (lactose synthetase A protein). *J. Biol. Chem.*, 256, 2701–2706.
9. Furukawa, K., Matsuta, K., Takeuchi, F., Kosuge, E., Miyamoto, T., and Kobata, A. (1990) Kinetic study of a galactosyltransferase in the B cells of patients with rheumatoid arthritis. *Int Immunol.*, 2, 105–112.
10. Gentzsch, M. and Tanner, W. (1996) The PMT gene family: protein O-glycosylation in *Saccharomyces cerevisiae* is vital. *EMBO J.*, 15, 5752–5759.
11. Hollis, G. F., Douglas, J. G., Shaper, N. L., Shaper, J. H., Stafford-Hollis, J. M., Evans, R. J., and Kirsch, I. R. (1989) Genomic structure of murine beta-1,4-galactosyltransferase. *Biochem Biophys Res Comm.*, 162, 1069–1075.
12. Keusch, J., Lydyard, P. M., Isenberg, D. A., and Delves, P. J. (1995) beta 1,4-Galactosyltransferase activity in B cells detected using a simple ELISA-based assay. *Glycobiology.*, 5, 365–700.
13. Kobata, A. (1992) Structures and functions of the sugar chains of glycoproteins. *Eur J Biochem.*, 209, 483–501.
14. Kozak, M. (1992) Regulation of translation in eukaryotic systems. *Ann Rev Cell Biol.*, 8, 197–225.
15. Lu, Q., Hasty, P., and Shur, B. D. (1997) Targeted mutation in beta 1,4-galactosyltransferase leads to pituitary insufficiency and neonatal lethality. *Develop Biol.*, 181, 257–267.
16. Malissard, M., Borsig, L., Di Marco, S., Grutter, M. G., Kragl, U., Wandrey, C., and Berger, E. G. (1996) Recombinant soluble beta-1,4-galactosyltransferases expressed in *Saccharomyces cerevisiae*. Purification, characterization and comparison with human enzyme. *Eur J Biochem.*, 239, 340–348.
17. Masri, K. A., Appert, H. E., and Fukuda, M. N. (1988) Identification of the full-length coding sequence for human galactosyltransferase (beta-N-acetylglucosaminide: beta 1,4-gactosyltransferase). *Biochem Biophys Res Comm.*, 157, 657–663.
18. Mengle-Gaw, L., McCoy-Haman, M. F., and Tiemeier, D. C. (1991) Genomic structure and expression of human beta-1,4-galactosyltransferase. *Biochem Biophys Res Comm.*, 176, 1269–1276.
19. Moscarello, M. A., Mitranic, M. M., and Vella, G. (1985) Stimulation of bovine milk gallctosyltransferase activity by bovine colostrum N-acetylglucosaminyltransferase I. *Biochem Biophys Acta.*, 831, 192–200.
20. Nakazawa, K., Ando, T., Kimura, T., and Narimatsu, H. (1988) Cloning and sequencing of a full-length cDNA of mouse N-acetylglucosamine (beta 14)galactosyltransferase. *J Biochem.*, 104, 165–168.
21. Nakazawa, K., Furukawa, K., Kobata, A., and Narimatsu, H. (1991) Characterization of a murine beta 1–4 galactosyltransferase expressed in COS-1 cells. *Eur J Biochem.*, 196, 363–368.
22. Narimatsu, H., Sinha, S., Brew, K., Okayama, H., and Qasba, P. K. (1986) Cloning and sequencing of cDNA of bovine N-acetylglucosamine (beta 1–4) galactosyltransferase. *Proc Natl Acad Sci USA.*, 83, 4720–4724.
23. Paquet, M. R. and Moscarello, M. A. (1984) A kinetic comparison of partially purified rat liver Golgi and rat serum galactosyltransferases. *Biochem J.*, 218, 745–751.

24. Powell, J. T. and Brew, K. (1974) The preparation and characterization of two forms of bovine galactosyl transferase. *Eur J Biochem.*, 48, 217–228.

25. Shaper, J. H., Joziasse, D. H., Meurer, J. A., Chou, T.-D. D., Schnaar, R. A., and Shaper, N. L. (1995) The Chicken genome contains two functional non-allelic β1,4-galactosyltransferase genes. *Glycoconjugate J.*, 12, 477.

26. Shaper, N. L., Shaper, J. H., Meuth, J. L., Fox, J. L., Chang, H., Kirsch, I. R., Hollis, and G. F. (1986) Bovine galactosyltransferase: identification of a clone by direct immunological screening of a cDNA expression library. *Proc Natl Acad Sci USA.*, 83, 1573–1577.

27. Shaper, N. L., Hollis, G. F., Douglas, J. G., Kirsch, I. R., and Shaper, J. H. (1988) Characterization of the full length cDNA for murine beta-1,4-galactosyltransferase. Novel features at the 5'-end predict two translational start sites at two in-frame AUGs. *J. Biol. Chem.*, 263, 10420–10428.

28. Shaper, N. L., Meurer, J. A., Joziasse, D. H., Chou, T. D., Smith, E. J., Schnaar, R. A., and Shaper, J. H. (1997) The Chicken Genome Contains Two Functional Nonallelic β1,4-Galactosyltransferase Genes: Chromosomal Assignment to Syntenic Regions Tracks Fate of the Two Gene Lineages in the Human Genome. *J. Biol. Chem.*, 272, 31389–31399.

29. Sheares, B. T. and Carlson, D. M. (1984) Two distinct UDP-galactose: 2-acetamido-2-deoxy-D-glucose 4 beta-galactosyltransferases in porcine trachea. *J. Biol. Chem.*, 259, 8045–8047.

30. Shur, B. D. (1982) Evidence that galactosyltransferase is a surface receptor for poly(N)-acetyllactosamine glycoconjugates on embryonal carcinoma cells. *J. Biol. Chem.*, 257, 6871–6878.

31. Wilson, I. B., Platt, F. M., Isenberg, D. A., and Rademacher, T. W. (1993) Aberrant control of galactosyltransferase in peripheral B lymphocytes and Epstein-Barr virus transformed B lymphoblasts from patients with rheumatoid arthritis [see comments]. *J Rheumatol.*, 20, 1282–1287.

What is claimed is:

1. An isolated nucleic acid which encodes a UDP-galactose: β-N-acetylglucosamine β-1,4-galactosyltransferase, herein said nucleic acid comprises the nucleotide sequence of nucleotides 1–1116 as set forth in SEQ ID NO:33 or a sequence-conservative variant thereof.

2. An isolated nucleic acid comprising nucleotides 94–1116 of SEQ ID NO:33, as depicted in SEQ ID NO:34.

3. A nucleic acid vector comprising the nucleic acid of claim 1.

4. A host cell comprising the nucleic acid vector of claim 3.

5. A nucleic acid vector comprising the nucleic acid of claim 2.

6. A host cell comprising the nucleic acid vector of claim 5.

7. An isolated nucleic acid which:

(i) encodes a UDP-galactose: β-N-acetylglucosamine β-1,4-galactosyltransferase which has a lower $K_m$ for UDP-galactose as a donor substrate than bovine β4Gal-T1; and (ii) hybridizes with SEQ ID NO:34 under conditions of high stringency.

8. A nucleic acid vector comprising the nucleic acid of claim 7.

9. The vector of claim 8, wherein said nucleic acid is operably linked to a transcriptional regulatory element.

10. A host cell comprising the vector of claim 9.

11. An isolated nucleic acid which:

(i) comprises a nucleic acid sequence selected from the group consisting of exons of a genomic DNA encoding for a UDP-galactose: β-N-acetylglucosamine β-1,4-galactosyltransferase which has a lower Km for UDP-galactose as a donor substrate than bovine β4Gal-T1, which exons have the nucleotide sequences of SEQ ID NO:11; SEQ ID NO:12; SEQ ID NO:13; SEQ ID NO:14; SEQ ID NO:15; and SEQ ID NO:16; and (ii) hybridizes with SEQ ID NO:34 under conditions of high stringency.

12. A nucleic acid vector comprising the nucleic acid of claim 11.

13. A host cell comprising the nucleic acid vector of claim 12.

14. A method for producing a UDP-galactose: β-N-acetylglucosamine β-1,4-galactosyltransferase polypeptide, which comprises:

(i) growing the host cell of claim 4 under conditions suitable for expression of the UDP-galactose: β-N-acetylglucosamine β-1,4-galactosyltransferase polypeptide; and (ii) isolating the UDP-galactose: β-N-acetylglucosamine β-1,4-galactosyltransferase polypeptide produced by the host cell.

15. A method for producing a UDP-galactose: β-N-acetylglucosamine β-1,4-galactosyltransferase polypeptide, which comprises:

(i) growing the host cell of claim 6 under conditions suitable for expression of the UDP-galactose: β-N-acetylglucosamine β-1,4-galactosyltransferase polypeptide; and (ii) isolating the UDP-galactose: β-N-acetylglucosamine β-1,4-galactosyltransferase polypeptide produced by the host cell.

16. The isolated nucleic acid of claim 7, wherein said nucleic acid is DNA.

17. The isolated nucleic acid of claim 16, wherein said DNA is cDNA.

18. The isolated nucleic acid of claim 16, wherein said DNA is genomic DNA.

* * * * *

SEQUENCE LISTING

<160> NUMBER OF SEQ ID NOS: 34

<210> SEQ ID NO 1
<211> LENGTH: 2027
<212> TYPE: DNA
<213> ORGANISM: Homo sapiens

<400> SEQUENCE: 1

```
agcctggtcc cagttggcct gccctgcttg tcgctgggat ctgaatgacc aaaccacttc     60

ccaccatggc tcctggaagg actaaatgaa gtcatgagta taaagtgctc ctgcatcgcc    120

agcagccgga tgcccgggcc cactgggcgg gccagtggcc gcttgcggga tgagcagact    180

gctggggggg acgctggagc gcgtctgcaa ggctgtgctc cttctctgcc tgctgcactt    240

cctcgtggcc gtcatcctct actttgacgt ctacgcccag cacctggcct tcttcagccg    300

cttcagtgcc cgaggccctg cccatgccct ccacccagct gctagcagca gcagcagcag    360

cagcaactgc tcccggccca acgccaccgc ctctagctcc gggctccctg aggtccccag    420

tgccctgccc ggtcccacgg ctcccacgct gccaccctgt cctgactcgc cacctggtct    480

tgtgggcaga ctgctgatcg agttcacctc acccatgccc ctggagcggg tgcagaggga    540

gaacccaggc gtgctcatgg gcggccgata cacaccgccc gactgcaccc cagcccagac    600

ggtggcggtc atcatcccct ttagacaccg ggaacaccac ctgcgctact ggctccacta    660

tctacacccc atcttgaggc ggcagcggct gcgctacggc gtctatgtca tcaaccagca    720

tggtgaggac accttcaacc gggccaagct gcttaacgtg ggcttcctag aggcgctgaa    780

ggaggatgcc gcctatgact gcttcatctt cagcgatgtg gacctggtcc ccatggatga    840

ccgcaaccta taccgctgcg gcgaccaacc ccgccacttt gccattgcca tggacaagtt    900

tggcttccgg cttccctatg ctggctactt tggaggtgtg tcaggcctga gtaaggctca    960

gtttctgaga atcaatggct tccccaatga gtactggggc tggggtggcg aggatgatga   1020

catcttcaac cggatctccc tgactgggat gaagatctca cgcccagaca tccgaatcgg   1080

ccgctaccgc atgatcaagc acgaccgcga caagcataac gaacctaacc ctcagaggtt   1140

taccaagatt caaaacacga agctgaccat gaagcgggac ggcattgggt cagtgcggta   1200

ccaggtcttg gaggtgtctc ggcaaccact cttcaccaat atcacagtgg acattgggcg   1260
```

-continued

```
gcctccgtcg tggccccctc ggggctgaca ctaatggaca gaggctctcg gtgccgaaga   1320

ttgcctgcca gaggactgac cacagcctgg ctggcagctg ctctgtggag gacctccagg   1380

actgagactg ggctctgttt tccaagggtc ttcactaggc cccctagcta cacctggaag   1440

tttcagaacc cactttgggg ggcctcctgc ctgggcaggc tcttcaagtg tggccctctt   1500

tggagtcaac cctccttccc gaccccctcc ccctagccca gccccagtca ctgtcagggt   1560

cgggccagcc cctgcactgc ctcgcagagt ggcctgggct aggtcactcc acctctctgt   1620

gcctcagttt cccccccttg agtcccctag ggcctggaag ggtgggaggt atgtctaggg   1680

ggcagtgtct cttccagggg gaattctcag ctcttgggaa ccccccttgct cccaggggag   1740

gggaaacctt tttcattcaa cattgtaggg ggcaagcttt ggtgcgcccc ctgctgagga   1800

gcagccccag gaggggacca gaggggatgc tgtgtcgctg cctgggatct tggggttggc   1860

ctttgcatgg gaggcaggtg ggcttggat cagtaagttt ggttcccgcc tccctgtttg   1920

agagaggagg caggagcccc agggccggct tgtgtttgta cattgcacag aaacttgtgt   1980

gggtgcttta gtaaaaaacg tgaatggaaa aaaaaaaaaa aaaaaaa                 2027
```

<210> SEQ ID NO 2
<211> LENGTH: 372
<212> TYPE: PRT
<213> ORGANISM: Homo sapiens

<400> SEQUENCE: 2

```
Met Ser Arg Leu Leu Gly Gly Thr Leu Glu Arg Val Cys Lys Ala Val
 1               5                  10                  15

Leu Leu Leu Cys Leu Leu His Phe Leu Val Ala Val Ile Leu Tyr Phe
            20                  25                  30

Asp Val Tyr Ala Gln His Leu Ala Phe Phe Ser Arg Phe Ser Ala Arg
        35                  40                  45

Gly Pro Ala His Ala Leu His Pro Ala Ala Ser Ser Ser Ser Ser Ser
    50                  55                  60

Ser Asn Cys Ser Arg Pro Asn Ala Thr Ala Ser Ser Ser Gly Leu Pro
65                  70                  75                  80

Glu Val Pro Ser Ala Leu Pro Gly Pro Thr Ala Pro Thr Leu Pro Pro
                85                  90                  95

Cys Pro Asp Ser Pro Pro Gly Leu Val Gly Arg Leu Leu Ile Glu Phe
            100                 105                 110

Thr Ser Pro Met Pro Leu Glu Arg Val Gln Arg Glu Asn Pro Gly Val
        115                 120                 125

Leu Met Gly Gly Arg Tyr Thr Pro Pro Asp Cys Thr Pro Ala Gln Thr
    130                 135                 140

Val Ala Val Ile Ile Pro Phe Arg His Arg Glu His His Leu Arg Tyr
145                 150                 155                 160

Trp Leu His Tyr Leu His Pro Ile Leu Arg Arg Gln Arg Leu Arg Tyr
                165                 170                 175

Gly Val Tyr Val Ile Asn Gln His Gly Glu Asp Thr Phe Asn Arg Ala
            180                 185                 190

Lys Leu Leu Asn Val Gly Phe Leu Glu Ala Leu Lys Glu Asp Ala Ala
        195                 200                 205

Tyr Asp Cys Phe Ile Phe Ser Asp Val Asp Leu Val Pro Met Asp Asp
    210                 215                 220

Arg Asn Leu Tyr Arg Cys Gly Asp Gln Pro Arg His Phe Ala Ile Ala
225                 230                 235                 240
```

-continued

```
Met Asp Lys Phe Gly Phe Arg Leu Pro Tyr Ala Gly Tyr Phe Gly Gly
                245                 250                 255

Val Ser Gly Leu Ser Lys Ala Gln Phe Leu Arg Ile Asn Gly Phe Pro
            260                 265                 270

Asn Glu Tyr Trp Gly Trp Gly Gly Glu Asp Asp Asp Ile Phe Asn Arg
        275                 280                 285

Ile Ser Leu Thr Gly Met Lys Ile Ser Arg Pro Asp Ile Arg Ile Gly
    290                 295                 300

Arg Tyr Arg Met Ile Lys His Asp Arg Asp Lys His Asn Glu Pro Asn
305                 310                 315                 320

Pro Gln Arg Phe Thr Lys Ile Gln Asn Thr Lys Leu Thr Met Lys Arg
                325                 330                 335

Asp Gly Ile Gly Ser Val Arg Tyr Gln Val Leu Glu Val Ser Arg Gln
            340                 345                 350

Pro Leu Phe Thr Asn Ile Thr Val Asp Ile Gly Arg Pro Pro Ser Trp
        355                 360                 365

Pro Pro Arg Gly
    370


<210> SEQ ID NO 3
<211> LENGTH: 342
<212> TYPE: PRT
<213> ORGANISM: Homo sapiens

<400> SEQUENCE: 3

Tyr Phe Asp Val Tyr Ala Gln His Leu Ala Phe Phe Ser Arg Phe Ser
 1               5                  10                  15

Ala Arg Gly Pro Ala His Ala Leu His Pro Ala Ala Ser Ser Ser Ser
            20                  25                  30

Ser Ser Ser Asn Cys Ser Arg Pro Asn Ala Thr Ala Ser Ser Ser Gly
        35                  40                  45

Leu Pro Glu Val Pro Ser Ala Leu Pro Gly Pro Thr Ala Pro Thr Leu
    50                  55                  60

Pro Pro Cys Pro Asp Ser Pro Pro Gly Leu Val Gly Arg Leu Leu Ile
65                  70                  75                  80

Glu Phe Thr Ser Pro Met Pro Leu Glu Arg Val Gln Arg Glu Asn Pro
                85                  90                  95

Gly Val Leu Met Gly Gly Arg Tyr Thr Pro Pro Asp Cys Thr Pro Ala
            100                 105                 110

Gln Thr Val Ala Val Ile Ile Pro Phe Arg His Arg Glu His His Leu
        115                 120                 125

Arg Tyr Trp Leu His Tyr Leu His Pro Ile Leu Arg Arg Gln Arg Leu
    130                 135                 140

Arg Tyr Gly Val Tyr Val Ile Asn Gln His Gly Glu Asp Thr Phe Asn
145                 150                 155                 160

Arg Ala Lys Leu Leu Asn Val Gly Phe Leu Glu Ala Leu Lys Glu Asp
                165                 170                 175

Ala Ala Tyr Asp Cys Phe Ile Phe Ser Asp Val Asp Leu Val Pro Met
            180                 185                 190

Asp Asp Arg Asn Leu Tyr Arg Cys Gly Asp Gln Pro Arg His Phe Ala
        195                 200                 205

Ile Ala Met Asp Lys Phe Gly Phe Arg Leu Pro Tyr Ala Gly Tyr Phe
    210                 215                 220

Gly Gly Val Ser Gly Leu Ser Lys Ala Gln Phe Leu Arg Ile Asn Gly
225                 230                 235                 240
```

-continued

```
Phe Pro Asn Glu Tyr Trp Gly Trp Gly Gly Glu Asp Asp Asp Ile Phe
                245                 250                 255

Asn Arg Ile Ser Leu Thr Gly Met Lys Ile Ser Arg Pro Asp Ile Arg
            260                 265                 270

Ile Gly Arg Tyr Arg Met Ile Lys His Asp Arg Asp Lys His Asn Glu
        275                 280                 285

Pro Asn Pro Gln Arg Phe Thr Lys Ile Gln Asn Thr Lys Leu Thr Met
    290                 295                 300

Lys Arg Asp Gly Ile Gly Ser Val Arg Tyr Gln Val Leu Glu Val Ser
305                 310                 315                 320

Arg Gln Pro Leu Phe Thr Asn Ile Thr Val Asp Ile Gly Arg Pro Pro
                325                 330                 335

Ser Trp Pro Pro Arg Gly
            340


<210> SEQ ID NO 4
<211> LENGTH: 400
<212> TYPE: PRT
<213> ORGANISM: Homo sapiens

<400> SEQUENCE: 4

Met Arg Leu Arg Glu Pro Leu Leu Ser Gly Ala Ala Met Pro Gly Ala
 1               5                  10                  15

Ser Leu Gln Arg Ala Cys Arg Leu Leu Val Ala Val Cys Val Trp His
            20                  25                  30

Leu Gly Val Thr Leu Val Tyr Tyr Leu Ala Gly Arg Asp Leu Ser Arg
        35                  40                  45

Leu Pro Gln Leu Val Gly Val Ser Thr Pro Leu Gln Gly Gly Ser Asn
    50                  55                  60

Ser Ala Ala Ala Ile Gly Gln Ser Ser Gly Glu Leu Arg Thr Gly Gly
65                  70                  75                  80

Ala Arg Pro Pro Pro Pro Leu Gly Ala Ser Ser Gln Pro Arg Pro Gly
                85                  90                  95

Gly Asp Ser Ser Pro Val Val Asp Ser Gly Pro Gly Pro Ala Ser Asn
            100                 105                 110

Leu Thr Ser Val Pro Val Pro His Thr Thr Ala Leu Ser Leu Pro Ala
        115                 120                 125

Cys Pro Glu Glu Ser Pro Leu Leu Val Gly Pro Met Leu Ile Glu Phe
    130                 135                 140

Asn Met Pro Val Asp Leu Glu Leu Val Ala Lys Gln Asn Pro Asn Val
145                 150                 155                 160

Lys Met Gly Gly Arg Tyr Ala Pro Arg Asp Cys Val Ser Pro His Lys
                165                 170                 175

Val Ala Ile Ile Ile Pro Phe Arg Asn Arg Gln Glu His Leu Lys Tyr
            180                 185                 190

Trp Leu Tyr Tyr Leu His Pro Val Leu Gln Arg Gln Gln Leu Asp Tyr
        195                 200                 205

Gly Ile Tyr Gly Ile Tyr Val Ile Asn Gln Ala Gly Asp Thr Ile Phe
    210                 215                 220

Asn Arg Ala Lys Leu Leu Asn Val Gly Phe Gln Glu Ala Leu Lys Asp
225                 230                 235                 240

Tyr Asp Tyr Thr Cys Phe Val Phe Ser Asp Val Asp Leu Ile Pro Met
                245                 250                 255

Asn Asp His Asn Ala Tyr Arg Cys Phe Ser Gln Pro Arg His Ile Ser
            260                 265                 270
```

-continued

```
Val Ala Met Asp Lys Phe Gly Phe Ser Leu Pro Tyr Val Gln Tyr Phe
        275                 280                 285

Gly Gly Val Ser Ala Leu Ser Lys Gln Gln Phe Leu Thr Ile Asn Gly
    290                 295                 300

Phe Pro Asn Asn Tyr Trp Gly Trp Gly Gly Glu Asp Asp Asp Ile Phe
305                 310                 315                 320

Asn Arg Leu Val Phe Arg Gly Met Ser Ile Ser Arg Pro Asn Ala Val
                325                 330                 335

Val Gly Arg Cys Arg Met Ile Arg His Ser Arg Asp Lys Lys Asn Glu
            340                 345                 350

Pro Asn Pro Gln Arg Phe Asp Arg Ile Ala His Thr Lys Glu Thr Met
        355                 360                 365

Leu Ser Asp Gly Leu Asn Ser Leu Thr Tyr Gln Val Leu Asp Val Gln
    370                 375                 380

Arg Tyr Pro Leu Tyr Thr Gln Ile Thr Val Asp Ile Gly Thr Pro Ser
385                 390                 395                 400


<210> SEQ ID NO 5
<211> LENGTH: 393
<212> TYPE: PRT
<213> ORGANISM: Homo sapiens

<400> SEQUENCE: 5

Met Leu Arg Arg Leu Leu Glu Arg Pro Cys Thr Leu Ala Leu Leu Val
 1               5                  10                  15

Gly Ser Gln Leu Ala Val Met Met Tyr Leu Ser Leu Gly Gly Phe Arg
            20                  25                  30

Ser Leu Ser Ala Leu Phe Gly Arg Asp Gln Gly Pro Thr Phe Asp Tyr
        35                  40                  45

Ser His Pro Arg Asp Val Tyr Ser Asn Leu Ser His Leu Pro Gly Ala
    50                  55                  60

Pro Gly Gly Pro Pro Ala Pro Gln Gly Leu Pro Tyr Cys Pro Glu Arg
65                  70                  75                  80

Ser Pro Leu Leu Val Gly Pro Val Ser Val Ser Phe Ser Pro Val Pro
                85                  90                  95

Ser Leu Ala Glu Ile Val Glu Arg Asn Pro Arg Val Glu Pro Gly Gly
            100                 105                 110

Arg Tyr Arg Pro Ala Gly Cys Glu Pro Arg Ser Arg Thr Ala Ile Ile
        115                 120                 125

Val Pro His Arg Ala Arg Glu His His Leu Arg Leu Leu Leu Tyr His
    130                 135                 140

Leu His Pro Phe Leu Gln Arg Gln Gln Leu Ala Tyr Gly Ile Tyr Val
145                 150                 155                 160

Ile His Gln Ala Gly Asn Gly Thr Phe Asn Pro Ala Lys Leu Leu Asn
                165                 170                 175

Val Gly Val Arg Glu Ala Leu Arg Asp Glu Glu Trp Asp Cys Leu Phe
            180                 185                 190

Leu His Asp Val Asp Leu Leu Pro Glu Asn Asp His Asn Leu Tyr Val
        195                 200                 205

Cys Asp Pro Arg Gly Pro Arg His Val Ala Val Ala Met Asn Lys Phe
    210                 215                 220

Gly Tyr Ser Leu Pro Tyr Pro Gln Tyr Phe Gly Gly Val Ser Ala Leu
225                 230                 235                 240

Thr Pro Asp Gln Tyr Leu Lys Met Asn Gly Phe Pro Asn Glu Tyr Trp
                245                 250                 255
```

-continued

```
Gly Trp Gly Gly Glu Asp Asp Asp Ile Ala Thr Arg Val Arg Leu Ala
            260                 265                 270

Gly Met Lys Ile Ser Arg Pro Pro Thr Ser Val Gly His Tyr Lys Met
        275                 280                 285

Val Lys His Arg Gly Asp Lys Gly Asn Glu Glu Asn Pro His Arg Phe
    290                 295                 300

Asp Leu Leu Val Arg Thr Gln Asn Ser Trp Thr Gln Asp Gly Met Asn
305                 310                 315                 320

Ser Leu Thr Tyr Gln Leu Leu Ala Arg Glu Leu Gly Pro Leu Tyr Thr
                325                 330                 335

Asn Ile Thr Ala Asp Ile Gly Thr Asp Pro Arg Gly Pro Arg Ala Pro
            340                 345                 350

Ser Gly Pro Arg Tyr Pro Pro Gly Ser Ser Gln Ala Phe Arg Gln Glu
        355                 360                 365

Met Leu Gln Arg Arg Pro Pro Ala Arg Pro Gly Pro Leu Ser Thr Ala
    370                 375                 380

Asn His Thr Ala Leu Arg Gly Ser His
385                 390


<210> SEQ ID NO 6
<211> LENGTH: 362
<212> TYPE: PRT
<213> ORGANISM: Gallus gallus

<400> SEQUENCE: 6

Met Lys Glu Pro Ala Leu Pro Gly Thr Ser Leu Gln Arg Ala Cys Arg
 1               5                  10                  15

Leu Leu Val Ala Phe Cys Ala Leu His Leu Ser Ala Thr Leu Leu Tyr
            20                  25                  30

Tyr Leu Ala Gly Ser Ser Leu Thr Pro Pro Arg Ser Pro Glu Pro Pro
        35                  40                  45

Pro Arg Arg Pro Pro Pro Ala Asn Leu Ser Leu Pro Pro Ser Arg Pro
    50                  55                  60

Pro Pro Pro Pro Ala Ala Arg Pro Arg Pro Gly Pro Val Ser Ala Gln
65                  70                  75                  80

Pro Arg Asn Leu Pro Asp Ser Ala Pro Ser Gly Leu Cys Pro Asp Pro
                85                  90                  95

Ser Pro Leu Leu Val Gly Pro Leu Arg Val Glu Phe Ser Gln Pro Val
            100                 105                 110

Asn Leu Glu Glu Val Ala Ser Thr Asn Pro Glu Val Arg Glu Gly Gly
        115                 120                 125

Arg Phe Ala Pro Lys Asp Cys Lys Ala Leu Gln Lys Val Ala Ile Ile
    130                 135                 140

Ile Pro Phe Arg Asn Arg Glu Glu His Leu Lys Tyr Trp Leu Tyr Tyr
145                 150                 155                 160

Met His Pro Ile Leu Gln Arg Gln Gln Leu Asp Tyr Gly Val Tyr Val
                165                 170                 175

Ile Asn Gln Asp Gly Asp Glu Glu Phe Asn Pro Ala Lys Leu Leu Asn
            180                 185                 190

Val Gly Phe Thr Glu Ala Leu Lys Glu Tyr Asp Tyr Asp Cys Phe Val
        195                 200                 205

Phe Ser Asp Val Asp Leu Ile Pro Met Asp Asp Arg Asn Thr Tyr Lys
    210                 215                 220

Cys Tyr Ser Gln Pro Arg His Leu Ser Val Ser Met Asp Lys Phe Gly
225                 230                 235                 240
```

-continued

```
Phe Arg Leu Pro Tyr Asn Gln Tyr Phe Gly Gly Val Ser Ala Leu Ser
                245                 250                 255

Lys Glu Gln Phe Thr Lys Ile Asn Gly Phe Pro Asn Asn Tyr Trp Gly
            260                 265                 270

Trp Gly Gly Glu Asp Asp Asp Ile Tyr Asn Arg Leu Val Phe Lys Gly
        275                 280                 285

Met Gly Ile Ser Arg Pro Asp Ala Val Ile Gly Lys Cys Arg Met Ile
    290                 295                 300

Arg His Ser Arg Asp Arg Lys Asn Glu Pro Asn Pro Glu Arg Phe Asp
305                 310                 315                 320

Arg Ile Ala His Thr Arg Glu Thr Met Ser Ser Asp Gly Leu Asn Ser
                325                 330                 335

Leu Ser Tyr Glu Val Leu Arg Thr Asp Arg Phe Pro Leu Tyr Thr Arg
            340                 345                 350

Ile Thr Val Asp Ile Gly Ala Pro Gly Ser
        355                 360


<210> SEQ ID NO 7
<211> LENGTH: 236
<212> TYPE: PRT
<213> ORGANISM: Gallus gallus

<400> SEQUENCE: 7

Met Thr Arg Leu Leu Leu Gly Val Thr Leu Glu Arg Ile Cys Lys Ala
 1               5                  10                  15

Val Leu Leu Leu Cys Leu Leu His Phe Val Ile Ile Met Ile Leu Tyr
            20                  25                  30

Phe Asp Val Tyr Ala Gln His Leu Asp Phe Phe Ser Arg Phe Asn Ala
        35                  40                  45

Arg Asn Thr Ser Arg Val His Pro Phe Ser Asn Ser Ser Arg Pro Asn
    50                  55                  60

Ser Thr Ala Pro Ser Tyr Gly Pro Arg Gly Ala Glu Pro Pro Ser Pro
65                  70                  75                  80

Ser Ala Lys Pro Asn Thr Asn Arg Ser Val Thr Glu Lys Pro Leu Gln
                85                  90                  95

Pro Cys Gln Glu Met Pro Ser Gly Leu Val Gly Arg Leu Leu Ile Glu
            100                 105                 110

Phe Ser Ser Pro Met Ser Met Glu Arg Val Gln Arg Glu Asn Pro Asp
        115                 120                 125

Val Ser Leu Gly Gly Lys Tyr Thr Pro Pro Asp Cys Leu Pro Arg Gln
    130                 135                 140

Lys Val Ala Ile Leu Ile Pro Phe Arg His Arg Glu His His Leu Lys
145                 150                 155                 160

Tyr Trp Leu His Tyr Leu His Pro Ile Leu Arg Arg Gln Lys Val Ala
                165                 170                 175

Tyr Asp Lys His Asn Glu Pro Asn Pro Gln Arg Phe Thr Lys Ile Gln
            180                 185                 190

Asn Thr Lys Met Thr Met Lys Arg Asp Gly Ile Ser Ser Leu Gln Tyr
        195                 200                 205

Arg Leu Val Glu Val Ser Arg Gln Pro Met Tyr Thr Asn Ile Thr Val
    210                 215                 220

Glu Ile Gly Arg Pro Pro Pro Arg Leu Ala Arg Gly
225                 230                 235
```

-continued

```
<210> SEQ ID NO 8
<211> LENGTH: 388
<212> TYPE: PRT
<213> ORGANISM: Lymnaea stagnalis

<400> SEQUENCE: 8

Met Tyr Leu Val Val Cys Trp Gly Arg Val Thr Gly Asn Met Ile Ser
 1               5                  10                  15

Thr Arg His Cys Phe Ser Arg Cys Lys Ser Arg Ser Val Arg Val Ile
            20                  25                  30

Lys Ala Thr Ala Met Leu Phe Val Ala Ala Met Leu Phe Leu Ala Leu
        35                  40                  45

His Met Asn Phe Ser His Glu Ala Ser Gln Gln Asn Leu His Arg Ala
    50                  55                  60

Ala Pro Ile Ser Ser Pro Thr Thr Ile Ser Arg Ser Thr Val Gln Ile
65                  70                  75                  80

Arg Asn Ala Thr His Asp Phe Leu Pro Ala Ser Ser Thr Pro Met Lys
                85                  90                  95

Asp Glu Leu Ile Glu Thr Glu Ser Glu Phe Val Asp Gly Phe Gln Arg
            100                 105                 110

Asn Glu Val Ile Ala Cys Ser Asp Thr Ser Glu Glu Phe Arg Thr Asp
        115                 120                 125

Ser Lys Arg Ile Thr Leu Val Asn Ser Gln Ser Gly Val Pro Cys Pro
    130                 135                 140

Ile Arg Pro Pro Ala Leu Ala Gly Arg Phe Val Pro Ser Lys Lys Ser
145                 150                 155                 160

Ser Thr Tyr His Glu Leu Ala Ala Met Phe Pro Asp Val Gln Asp Gly
                165                 170                 175

Gly His Tyr Thr Pro Arg Met Cys Thr Pro Ala Glu Lys Thr Ala Ile
            180                 185                 190

Ile Ile Pro Tyr Arg Asn Arg Cys Arg His Leu Tyr Thr Leu Leu Pro
        195                 200                 205

Asn Leu Ile Pro Met Leu Met Arg Gln Asn Val Asp Phe Gly Gly Glu
    210                 215                 220

Asp Asp Asp Leu Arg Asn Arg Ala Val His Met Lys Leu Pro Leu Leu
225                 230                 235                 240

Arg Lys Thr Leu Ala His Gly Leu Tyr Asp Met Val Ser His Val Glu
                245                 250                 255

Ala Gly Trp Asn Val Asn Pro His Ser Lys Gly Ala His Ser Leu Tyr
            260                 265                 270

Asp Met Leu Asn Lys Ala Leu Gly Val Gln Ala Gly Trp Asn Val His
        275                 280                 285

Pro Asn Ser Lys Trp Pro Leu Arg Leu Phe Asp Ser Val Asn His Ala
    290                 295                 300

Pro Ala Glu Gly Ala Gly Trp Asn Val Asn Pro Asp Arg Phe Lys Ile
305                 310                 315                 320

Tyr Ser Thr Ser Arg Gln Arg Gln His Val Asp Gly Ile Asn Ser Leu
                325                 330                 335

Val Tyr Asn Val Thr Trp Tyr Arg Thr Ser Pro Leu Tyr Thr Trp Val
            340                 345                 350

Gly Val Gly Phe Asn Lys Thr Val Ile Thr Asn Ser Ile Pro Glu Asp
        355                 360                 365
```

-continued

```
Leu Arg Ile Gly Pro Glu Ala Asp Asn Thr Tyr Leu Thr Gly Asn Phe
    370                 375                 380

Thr Ile Ile Ser
385
```

<210> SEQ ID NO 9
<211> LENGTH: 21
<212> TYPE: DNA
<213> ORGANISM: Homo sapiens

<400> SEQUENCE: 9

```
tactttgacg tctacgccca g                                               21
```

<210> SEQ ID NO 10
<211> LENGTH: 22
<212> TYPE: DNA
<213> ORGANISM: Homo sapiens

<400> SEQUENCE: 10

```
ctgagactgg gctcttgttt tc                                              22
```

<210> SEQ ID NO 11
<211> LENGTH: 313
<212> TYPE: DNA
<213> ORGANISM: Homo sapiens

<400> SEQUENCE: 11

```
atgagcagac tgctgggggg gacgctggag cgcgtctgca aggctgtgct ccttctctgc      60

ctgctgcact tcctcgtggc cgtcatcctc tactttgacg tctacgccca gcacctggcc     120

ttcttcagcc gcttcagtgc ccgaggccct gcccatgccc tccacccagc tgctagcagc     180

agcagcagca gcagcaactg ctcccggccc aacgccaccg cctctagctc cgggctccct     240

gaggtcccca gtgccctgcc cggtcccacg gctcccacgc tgccaccctg tcctgactcg     300

ccacctggtc ttg                                                        313
```

<210> SEQ ID NO 12
<211> LENGTH: 236
<212> TYPE: DNA
<213> ORGANISM: Homo sapiens

<400> SEQUENCE: 12

```
tgggcagact gctgatcgag ttcacctcac ccatgcccct ggagcgggtg cagagggaga      60

acccaggcgt gctcatgggc ggccgataca caccgcccga ctgcacccca gcccagacgg     120

tggcggtcat catccccttt agacaccggg aacaccacct gcgctactgg ctccactatc     180

tacaccccat cttgaggcgg cagcggctgc gctacggcgt ctatgtcatc aaccag         236
```

<210> SEQ ID NO 13
<211> LENGTH: 191
<212> TYPE: DNA
<213> ORGANISM: Homo sapiens

<400> SEQUENCE: 13

```
catggtgagg acaccttcaa ccgggccaag ctgcttaacg tgggcttcct agaggcgctg      60

aaggaggatg ccgcctatga ctgcttcatc ttcagcgatg tggacctggt ccccatggat     120

gaccgcaacc tataccgctg cggcgaccaa ccccgccact ttgccattgc catggacaag     180

tttggcttcc g                                                          191
```

-continued

<210> SEQ ID NO 14
<211> LENGTH: 123
<212> TYPE: DNA
<213> ORGANISM: Homo sapiens

<400> SEQUENCE: 14
gcttccctat gctggctact ttggaggtgt gtcaggcctg agtaaggctc agtttctgag 60
aatcaatggc ttccccaatg agtactgggg ctggggtggc gaggatgatg acatcttcaa 120
ccg 123

<210> SEQ ID NO 15
<211> LENGTH: 105
<212> TYPE: DNA
<213> ORGANISM: Homo sapiens

<400> SEQUENCE: 15
gatctccctg actgggatga agatctcacg cccagacatc cgaatcggcc gctaccgcat 60
gatcaagcac gaccgcgaca agcataacga acctaaccct cagag 105

<210> SEQ ID NO 16
<211> LENGTH: 148
<212> TYPE: DNA
<213> ORGANISM: Homo sapiens

<400> SEQUENCE: 16
gtttaccaag attcaaaaca cgaagctgac catgaagcgg gacggcattg ggtcagtgcg 60
gtaccaggtc ttggaggtgt ctcggcaacc actcttcacc aatatcacag tggacattgg 120
gcggcctccg tcgtggcccc ctcggggc 148

<210> SEQ ID NO 17
<211> LENGTH: 18
<212> TYPE: DNA
<213> ORGANISM: Homo sapiens

<400> SEQUENCE: 17
cagcagccgg atgcccgg 18

<210> SEQ ID NO 18
<211> LENGTH: 18
<212> TYPE: DNA
<213> ORGANISM: Homo sapiens

<400> SEQUENCE: 18
cccacaggca ggccatac 18

<210> SEQ ID NO 19
<211> LENGTH: 21
<212> TYPE: DNA
<213> ORGANISM: Homo sapiens

<400> SEQUENCE: 19
gattcctgac actgtcctgt c 21

<210> SEQ ID NO 20
<211> LENGTH: 18
<212> TYPE: DNA
<213> ORGANISM: Homo sapiens

<400> SEQUENCE: 20
ccaacaggca catggacc 18

-continued

```
<210> SEQ ID NO 21
<211> LENGTH: 21
<212> TYPE: DNA
<213> ORGANISM: Homo sapiens

<400> SEQUENCE: 21

ggagagtggc aaaagggcag g                                           21


<210> SEQ ID NO 22
<211> LENGTH: 21
<212> TYPE: DNA
<213> ORGANISM: Homo sapiens

<400> SEQUENCE: 22

ggctgggtcc agctgagaag a                                           21


<210> SEQ ID NO 23
<211> LENGTH: 20
<212> TYPE: DNA
<213> ORGANISM: Homo sapiens

<400> SEQUENCE: 23

ggacccttac tgacacctgc                                             20


<210> SEQ ID NO 24
<211> LENGTH: 17
<212> TYPE: DNA
<213> ORGANISM: Homo sapiens

<400> SEQUENCE: 24

ccccaccgcg tgcttac                                                17


<210> SEQ ID NO 25
<211> LENGTH: 21
<212> TYPE: DNA
<213> ORGANISM: Homo sapiens

<400> SEQUENCE: 25

cctggagcct gttccagtct g                                           21


<210> SEQ ID NO 26
<211> LENGTH: 18
<212> TYPE: DNA
<213> ORGANISM: Homo sapiens

<400> SEQUENCE: 26

gaagttgcct ctggggag                                               18


<210> SEQ ID NO 27
<211> LENGTH: 21
<212> TYPE: DNA
<213> ORGANISM: Homo sapiens

<400> SEQUENCE: 27

gtggaccatt tccatcctat c                                           21


<210> SEQ ID NO 28
<211> LENGTH: 29
<212> TYPE: DNA
<213> ORGANISM: Homo sapiens

<400> SEQUENCE: 28

atggatccga aaacagagcc cagtctcag                                   29
```

-continued

<210> SEQ ID NO 29
<211> LENGTH: 23
<212> TYPE: DNA
<213> ORGANISM: Homo sapiens

<400> SEQUENCE: 29
tgaaggagga tgccgcctat gac 23

<210> SEQ ID NO 30
<211> LENGTH: 21
<212> TYPE: DNA
<213> ORGANISM: Homo sapiens

<400> SEQUENCE: 30
gaaactgagc cttactcagg c 21

<210> SEQ ID NO 31
<211> LENGTH: 22
<212> TYPE: DNA
<213> ORGANISM: Homo sapiens

<400> SEQUENCE: 31
tccacatcgc tgaagatgaa gc 22

<210> SEQ ID NO 32
<211> LENGTH: 27
<212> TYPE: DNA
<213> ORGANISM: Homo sapiens

<400> SEQUENCE: 32
agcggatcca tgagcagact gctgggg 27

<210> SEQ ID NO 33
<211> LENGTH: 1116
<212> TYPE: DNA
<213> ORGANISM: Homo sapiens

<400> SEQUENCE: 33
atgagcagac tgctgggggg gacgctggag cgcgtctgca aggctgtgct ccttctctgc 60
ctgctgcact tcctcgtggc cgtcatcctc tactttgacg tctacgccca gcacctggcc 120
ttcttcagcc gcttcagtgc ccgaggccct gcccatgccc tccacccagc tgctagcagc 180
agcagcagca gcagcaactg ctcccggccc aacgccaccg cctctagctc cgggctccct 240
gaggtcccca gtgccctgcc cggtcccacg gctcccacgc tgccaccctg tcctgactcg 300
ccacctggtc ttgtgggcag actgctgatc gagttcacct cacccatgcc cctggagcgg 360
gtgcagaggg agaacccagg cgtgctcatg ggcggccgat acacaccgcc cgactgcacc 420
ccagcccaga cggtggcggt catcatcccc tttagacacc gggaacacca cctgcgctac 480
tggctccact atctacaccc catcttgagg cggcagcggc tgcgctacgg cgtctatgtc 540
atcaaccagc atggtgagga caccttcaac cgggccaagc tgcttaacgt gggcttccta 600
gaggcgctga aggaggatgc cgcctatgac tgcttcatct tcagcgatgt ggacctggtc 660
cccatggatg accgcaacct ataccgctgc ggcgaccaac cccgccactt tgccattgcc 720
atggacaagt ttggcttccg gcttccctat gctggctact ttggaggtgt gtcaggcctg 780
agtaaggctc agtttctgag aatcaatggc ttccccaatg agtactgggg ctggggtggc 840
gaggatgatg acatcttcaa ccggatctcc ctgactggga tgaagatctc acgcccagac 900
atccgaatcg gccgctaccg catgatcaag cacgaccgcg acaagcataa cgaacctaac 960

-continued

```
cctcagaggt ttaccaagat tcaaaacacg aagctgacca tgaagcggga cggcattggg   1020

tcagtgcggt accaggtctt ggaggtgtct cggcaaccac tcttcaccaa tatcacagtg   1080

gacattgggc ggcctccgtc gtggcccccct cggggc                            1116


<210> SEQ ID NO 34
<211> LENGTH: 1023
<212> TYPE: DNA
<213> ORGANISM: Homo sapiens

<400> SEQUENCE: 34

tttgacgtct acgcccagca cctggccttc ttcagccgct tcagtgcccg aggccctgcc     60

catgccctcc acccagctgc tagcagcagc agcagcagca gcaactgctc ccggcccaac    120

gccaccgcct ctagctccgg gctccctgag gtccccagtg ccctgcccgg tcccacggct    180

cccacgctgc caccctgtcc tgactcgcca cctggtcttg tgggcagact gctgatcgag    240

ttcacctcac ccatgcccct ggagcgggtg cagagggaga acccaggcgt gctcatgggc    300

ggccgataca caccgcccga ctgcacccca gcccagacgg tggcggtcat catccccttt    360

agacaccggg aacaccacct gcgctactgg ctccactatc tacaccccat cttgaggcgg    420

cagcggctgc gctacggcgt ctatgtcatc aaccagcatg gtgaggacac cttcaaccgg    480

gccaagctgc ttaacgtggg cttcctagag gcgctgaagg aggatgccgc ctatgactgc    540

ttcatcttca gcgatgtgga cctggtcccc atggatgacc gcaacctata ccgctgcggc    600

gaccaacccc gccactttgc cattgccatg gacaagtttg gcttccggct tccctatgct    660

ggctactttg gaggtgtgtc aggcctgagt aaggctcagt ttctgagaat caatggcttc    720

cccaatgagt actggggctg gggtggcgag gatgatgaca tcttcaaccg gatctccctg    780

actgggatga agatctcacg cccagacatc cgaatcggcc gctaccgcat gatcaagcac    840

gaccgcgaca agcataacga acctaaccct cagaggttta ccaagattca aaacacgaag    900

ctgaccatga agcgggacgg cattgggtca gtgcggtacc aggtcttgga ggtgtctcgg    960

caaccactct tcaccaatat cacagtggac attgggcggc ctccgtcgtg gccccctcgg   1020

ggc                                                                 1023
```